United States Patent [19]

Colin

[11] Patent Number: 5,269,891
[45] Date of Patent: Dec. 14, 1993

[54] METHOD AND APPARATUS FOR DETERMINATION OF A CONSTITUENT IN A FLUID

[75] Inventor: Fernand J. G. Colin, Watermael-Boitsfort, Belgium

[73] Assignee: Novo Nordisk A/S, Denmark

[21] Appl. No.: 9,343

[22] Filed: Jan. 26, 1993

Related U.S. Application Data

[63] Continuation of Ser. No. 752,690, Oct. 7, 1991, filed as PCT/DK90/00067, Mar. 9, 1990, abandoned.

[30] Foreign Application Priority Data

Mar. 9, 1989 [DK] Denmark .............................. 1159/89

[51] Int. Cl.$^5$ ............................................ G01N 27/26
[52] U.S. Cl. ................................ 204/153.12; 204/402; 204/403; 204/435
[58] Field of Search .................... 204/402, 403, 153.12, 204/435

[56] References Cited

U.S. PATENT DOCUMENTS

| | | | |
|---|---|---|---|
| 4,545,382 | 10/1985 | Higgins et al. | 204/403 |
| 4,576,704 | 3/1986 | Chiusole et al. | 204/402 |
| 4,711,245 | 12/1987 | Higgins et al. | 204/403 |
| 4,758,323 | 7/1988 | Davis et al. | 204/403 |
| 4,820,399 | 4/1989 | Senda et al. | 204/403 |

FOREIGN PATENT DOCUMENTS

| | | |
|---|---|---|
| 125137 | 11/1984 | European Pat. Off. . |
| 127958 | 12/1984 | European Pat. Off. . |
| 234938 | 9/1987 | European Pat. Off. . |
| 251915 | 1/1988 | European Pat. Off. . |
| 78636 | 4/1988 | European Pat. Off. . |
| 184909 | 6/1988 | European Pat. Off. . |
| 351891 | 1/1990 | European Pat. Off. . |
| WO 89/10395 | 11/1989 | France . |
| 1223363 | 2/1971 | United Kingdom . |

OTHER PUBLICATIONS

Yu. Yu. Kulis; "Analytical Systems on the Basis of Immobilised Enzymes-4.5 Manufacturing and Using Glucose Enzyme Electrodes" (undated).
Brinina H. Z.; Neyman Ye. Ya., Slepushkin V. V.; "Inversion Electroanalitical Methods"; p. 60 (undated).
Kulis Yu. Yu., Razumas V. Y.; "Bioamperemetry"; (undated).
Analytical Chemistry 62, 1990.

*Primary Examiner*—John Niebling
*Assistant Examiner*—Bruce F. Bell
*Attorney, Agent, or Firm*—Willian Brinks Olds Hofer Gilson & Lione

[57] ABSTRACT

A method is provided for measuring the concentration of a constituent of a fluid sample, e.g. glucose in a glucose-containing blood sample, by means of an electrode device. Also provided are an electrode device comprising the electrodes used in the method, a sensor electrode for use in the method, and an apparatus for use in the measurement of the concentration of the constituent in the sample.

47 Claims, 22 Drawing Sheets

METHOD AND APPARATUS FOR DETERMINATION OF A CONSTITUENT IN A FLUID

This application is a continuation of application Ser. No. 07/752,690, filed Oct. 7, 1991, filed as PCT/DK90/00067, Mar. 9, 1990, now abandoned.

FIELD OF THE INVENTION

The present invention relates to a method for measuring the concentration of at least one constituent of a fluid sample, e.g., glucose in a glucose-containing aqueous medium, for example a body fluid, in particular a whole blood sample, to an electrode device comprising the electrodes used in the measurement of the concentration of the constituent, to a sensor electrode for use in the method according to the invention and to an apparatus for use in the measurement of the concentration of the constituent in the sample, the apparatus preferably being portable.

DESCRIPTION OF PRIOR ART

Electrode devices and methods for detecting the amount of selected compounds in a liquid mixture are known in the art. Thus, in EP 78,636B and in EP 125,137A a sensor electrode for in vivo measurement of the amount of a component in a liquid mixture is described, wherein a charge-transfer mediator, such as ferrocene, is used as charge-transfer mediator in an enzyme-catalyzed reaction to transfer electrons arising from the reaction between the enzyme and a component in the liquid. The charge-transfer mediator ferrocene is adhered to the surface of the electrode in the form of a thin film layer or strip, for example by deposition from a solution. This known device suffers from severe drawbacks, i.e. the charge-transfer mediator will during the measurement rather rapidly be depleted from the strip causing a degradation of measurement reproducibility as explained into more details later. A similar device is described in EP 127,958A. The electrode devices are preferably intended for in vivo measurement of glucose in blood.

WO 89/10395 describes an enzyme electrode comprising a matrix made from a conductive powder, an enzyme and a charge-transfer mediator. The device suffers from the drawback that the concentration of the charge-transfer mediator is rather low. It is therefore necessary to operate the electrode at a rather high applied potential, leading to interference from other oxidizable substances in the sample.

The present invention provides an electrode device which eliminates the drawbacks of the prior art electrode devices.

SUMMARY OF THE INVENTION

The present invention provides a method of measuring at least one constituent of a fluid sample by means of an electrode device including at least one measuring electrode having an exposed surface part at a free end portion of the electrode device and extending longitudinally through said end portion, said method comprising removing an outer end section of the free end portion so as to provide a new exposed surface part of the measuring electrode, and subsequently exposing said exposed surface part of the measuring electrode to a sample of said fluid, so as to generate a measuring signal representative of said constituent of the sample. When the exposed surface part of the measuring electrode or electrodes has been exposed to a first fluid sample for measuring a constituent thereof, part of the fluid sample will inevitably adhere to the exposed surface part. In order to avoid contamination of the next fluid sample to be measured it is necessary to secure that any residue of the first sample is efficiently removed. Furthermore, a fresh sensor electrode surface is also desirable to ensure reproducibility of measurements. This is obtained by the method according to the invention in which a new exposed surface part of the measuring electrode or electrodes is provided each time a measurement is to be made on a new fluid sample, namely by removing an outer end section of the free end portion of the electrode or electrodes.

Such an outer end section may be removed by means of any suitable too. In a preferred embodiment, however, the electrode device is arranged in a measurement apparatus with the exposed surface part of the measuring electrode in an exposed position, said measuring device including an electronic measuring circuitry for receiving said measuring signal or signals, the electrode device being moved longitudinally outwardly by an increment for each measurement to be made, and the outer end section of the electrode device being subsequently removed by means of removing means mounted movably on the measuring apparatus. The measuring circuitry of the measuring apparatus is electrically connected to the electrode or electrodes of the electrode device when the electrode device is arranged in the measuring apparatus, so that the measuring circuitry may receive and process the measuring signals received from the electrode or electrodes, and the result of the measurement made may, for example, be displayed directly on a visual display of the measuring apparatus. Each time a measurement has been made, the electrode device may be moved longitudinally outwardly by an increment corresponding to the thickness of the outer end section to be removed from the free end portion of the electrode device. Thereafter, the outer end section of the electrode device may be removed by moving the removing means in relation to the measuring apparatus.

The removing means for removing the free end section of the outer end portion of the electrode device may be of any suitable type and may, for example, comprise grinding or abrasion means. Alternatively, the free end portion of the electrode device may be divided into longitudinal sections by cross-sectional areas defining predetermined fracture surfaces. In that case, the removing means may comprise impact means or bending means for causing fracture along the outermost of the predetermined fracture surfaces.

In a preferred embodiment, however, the free end portion of the electrode device is removed by cutting, for example by means of a milling cutter or by means of a single cutting blade. Preferably, a thin slice is cut from the outer end portion of the electrode device, for example by means of cutting means formed like the blade of a plane.

It should be understood that the end surface of the electrode device formed by removing an outer end section therefrom may be convexly or concavely curved or may have a concave or convex conical or frustoconical shape. In the latter case the removing means may operate like a pencil sharpener. In a preferred embodiment, however, the end surface of the electrode device including the exposed surface part of the electrode or electrodes is substantially plane.

The method according to the invention may be used for measuring the concentration of a constituent of gaseous and liquid fluid samples of any type. Specifically, the method according to the invention may be used for such measurements on fluid samples within the medical and veterinary field. Thus, the fluid samples, may, e.g., be a sample of an animal or human body fluids, such as whole blood. The method according to the invention is especially useful in connection with the measurement of the content of glucose in blood.

The method according to the invention may be used for measuring the concentration of glucose in body fluids, such as whole blood, blood plasma, serum, urine or saliva, in particular in whole blood, by use of a reliable and reproducible in vitro method according to the invention which method is based on a novel electrochemical principle using a charge-transfer mediator present in a non-polar medium in a sensor electrode which operates at a constant potential which is sufficiently low to substantially avoid interference resulting from oxidation of other oxidizable substances, such as acetylsalicylic acid (aspirin), paracetamol (acetaminophen), ascorbic acid, and sulfonylureas (tolbutamide, glibenclamide), present in the aqueous sample, such as a sample of a body fluid, in particular a whole blood sample.

In one aspect, the present invention relates to a method for determining glucose in a sample of an aqueous medium, the method being advantageous in that a substantially specific measure of the concentration of glucose is obtained without any significant uncertainty arising from a co-determination of interfering substances which, in general, can be present in the aqueous medium, in particular in blood. The method is based on monitoring the flow of current at an electrically conductive sensor electrode when a glucose oxidase catalyzes a redox reaction of glucose in the presence of a charge-transfer mediator, preferably a ferrocene derivative, such as 1,1'-dimethylferrocene.

According to another aspect, the present invention provides an electrode device for use in the method described above, said electrode device comprising an electrode body member (electrode device body) having a free end portion, and at least one measuring or sensor electrode extending axially through said end portion and having a substantially uniform cross-sectional area within said end portion. Because the cross-sectional area of each of the sensor or measuring electrodes positioned in the free end portion of the electrode body member is substantially uniform, the exposed active surface area of each electrode remains substantially unchanged when an outer end section or slice is removed from the free end portion. The electrode body member in which the measuring electrode is embedded may in itself define an outer electrode provided that this outer electrode is sufficiently electrically insulated from the other inner electrode or electrodes. In the preferred embodiment, the electrode device is substantially linear. The electrode device may, however, be curved and may, for example, define an arc of a circle.

In a preferred aspect, the invention relates to an electrode device comprising an electrode device body, a sensor electrode, a reference electrode and a suitable counter electrode. The electrodes are suitably positioned in separate channels in the electrode device body, the electrode device body preferably having the shape of a cylindrical rod, and the electrode channels preferably being longitudinally disposed in the electrode device body.

In preferred aspect, the body of the electrode device is made of a sliceable polymeric material and the sensor electrode ingredients are uniformly dispersed in a substantially water-insoluble carrier medium and uniformly distributed throughout the channels in the form of sliceable, high-viscosity paste. As will be explained in greater detail in the following, this construction permits the reuse of the electrode device for a number of determinations, a fresh sensing surface being provided before each determination by e.g. cutting away a cross-sectional slice. The measurement is performed by bringing a surface of the electrode device, the surface suitably corresponding to a cross section of the electrode device, such as a perpendicular cross section, and comprising cross sections of all of the electrodes present, into contact with a sample of the aqueous medium, the sample preferably being a sample of body fluid, in particular a drop of whole blood, which is taken from a patient, preferably by the patient himself, substantially immediately before the measurement is to be made. Before every measurement, the sensing surface of the electrode device is renewed by cutting off a thin slice of the electrode device in order to ensure the removal of any contaminants present on the sensing surface and to provide a fresh sensing surface of the electrode device. In addition, the removal of the sensor electrode sensing surface which has been exposed to the aqueous medium in question during the preceding measurement serves to ensure that the required amount of glucose oxidase and charge-transfer mediator is present at the surface of the electrode(s). Thus, a reliable and reproducible determination of the glucose concentration in a sample of an aqueous medium, such as a sample of body fluid, in particular a whole blood sample, without any interference present from contaminants from earlier measurements is obtained.

In principle, each electrode may be connected to the electrode body member in any suitable manner and may, for example, be attached to the outer peripheral surface of the electrode body member. Preferably, each electrode is received in a bore (channel) extending longitudinally through the free end portion of the electrode body member, whereby the electrode is embedded in and protected by the electrode body member.

Each electrode may be rod-shaped and may be fastened in each respective bore, for example by means of an adhesive. Alternatively, at least one of the electrodes may be moulded in the bore by introducing a paste-like electrode material into the bore.

The present invention also provides a measuring apparatus for use in the method described above, said apparatus comprising an apparatus body member defining an outwardly open cavity for receiving the electrode device therein, removing means mounted on the body member so as to be movable in relation thereto along a path intersecting said cavity for removing said outer end section from the free end portion of an electrode device received in the cavity, an electronic measuring circuitry for processing measuring signals. received from the electrode or electrodes of the electrode device, and connecting means for electrically connecting the electrode or electrodes of the electrode device to the electronic measuring circuitry when the electrode device is received in said cavity. The measuring apparatus may be made in pocket size so that it may be carried by a patient, such as a diabetic, who may use the apparatus for currently testing of the glucose content of his or hers blood. When an electrode device has been positioned in the cavity of the apparatus and the electrode of the electrode device has been connected to the electronic measuring circuitry of the apparatus, such electrode device may be used for measuring or testing a plurality of blood samples. When a test or measurement has been made, the removing means are operated so as to remove the outer end section from the free end portion of the electrode device. The apparatus preferably comprises means for moving the electrode device outwardly by an increment each time the removing means has been operated so that the exposed active surface part of each of the electrodes is always in substantially the same position in relation to the apparatus when a measurement is being made. As indicated above, the end surface of the electrode device may be concavely curved. Thus, the end surface of the electrode device may in itself and/or in combination with adjacent wall parts of the measuring apparatus define a cup-shaped container for receiving a liquid sample such as a drop of blood to be tested.

The removing means may, for example, comprise a motor driven grinding wheel or other kinds of grinding or abrasion means. Preferably, however, the removing means define at least one cutting edge for cutting the outer end section from the outer end portion of the electrode device when the removing means are moved along said path. Thus, the removing means may comprise a motor driven milling cutter or a plane iron functioning like a cheese knife. The said cutting edge or edges may be rectilinear or convexly or concavely curved.

The removing means which may comprise a rotating grinding wheel, a rotating miller or cutter, a plane or curved abrasive surface, or a plane iron or cutting blade may be mounted so as to be movable reciprocatingly along said path. Alternatively, the removing means may be mounted on the apparatus body member so as to be rotatable in relation thereto. When in the latter case the removing means comprises a cutting blade, the removing means may be formed like a pencil sharpener or comprise a cutting knife functioning like that of a bread slicer. It should be understood that the removing means could also be of the non-mechanical type and could comprise means for cutting the outer end section from the free end portion of the electrode device by means of a laser beam or similar non-mechanical cutting means.

When the removing means are mounted rotatably in relation to the apparatus body member, the apparatus may further comprise means for permitting rotation of the removing means in one direction only, and such rotation permitting means may, for example, comprise a ratchet mechanism.

The moving means for incrementally moving the electrode device outwardly in the cavity of the measuring apparatus each time the removing means have been operated may comprise a driving member driven by the movement of said removing means. Thus, the reciprocating or rotating movement of the removing means automatically causes that the electrode device is moved outwardly by an increment corresponding to the thickness of the end section or slice to be removed from the free end portion of the electrode device.

The removing means may be mounted on a lid-like member which is movable to a closing, non-operative position in which said exposed surface part of the measuring electrode or electrodes is covered and protected by the like-like member, so that the active exposed electrode surface part is well protected when the measuring apparatus is carried, for example in pocket or a hand bag.

When the apparatus is used for measuring a constituent, such a glucose, in the blood of a patient, such as a diabetic, the apparatus preferably further comprises a skin puncturing member mounted in the apparatus body member so as to be movable between retracted and extended positions, biassing means for biassing the puncturing member toward its extended position, and releasable locking means for retaining the puncturing member in its retracted position against the bias of the biassing means, whereby the puncturing member may perform a sudden skin puncturing movement from its retracted to its extended position, when the locking means are released. The apparatus may comprise a skin contacting surface, and the puncturing member may be arranged totally within the apparatus body member or housing in its retracted position, while the puncturing member may protrude from the skin contacting surface of the apparatus in its extended position. When the apparatus is to be used, the patient may place the tip of his finger or another skin surface part in contact with the skin contacting surface of the apparatus, whereafter the locking means may be released. When the skin of the patient has been punctured, the patient may apply a drop of blood to the exposed end surface of the electrode device.

The apparatus may also comprise a visual display for displaying the result of the measurement performed by the electrode or electrodes of the electrode device, so that the result or results of each measurement may be directly read from the display.

The apparatus according to the invention can preferably be used for determining the concentration of glucose in an aqueous medium, the apparatus comprising an electrode device containing a sensor electrode, the apparatus preferably being portable and well suited for use by patients suffering from diabetes in order to self-monitor the glucose level in a body fluid, in particular in whole blood. Furthermore, certain embodiments of the apparatus of the invention are particularly useful as a diagnostic tool in hospital wards for intensive care of therapy, or in internal or general medicine as well as in veterinary medicine.

DETAILED DISCLOSURE OF THE INVENTION

Description of the principle of the preferred method according to the invention

The basis of the preferred method according to the invention for measuring the concentration of glucose in a sample of a glucose-containing aqueous medium, which can be performed by means of an apparatus comprising an electrode device according to the present invention, is the reaction between glucose and the enzyme glucose oxidase (GOD). Electrons produced by this oxidation reaction are transferred to a charge-transfer mediator, e.g. a metallocene or a derivative thereof, and finally captured by a conductive material in the sensor electrode, e.g. graphite particles. The latter enzyme-catalyzed oxidation of glucose leads to gluconic acid and the "reduced form" of glucose oxidase, i.e. glucose oxidase wherein at least one functional group has been reduced. This reduced enzyme reacts with the oxidized form of the charge-transfer mediator, which is formed by donation of an electron from the "reduced" form of the charge-transfer mediator to the electrically conductive sensor electrode, and the glucose oxidase is thereby regenerated together with the reduced form of the charge-transfer mediator. The electrical current produced in the process is proportional to the concentration of glucose present in the sample.

The reactions can schematically be described by the following equations:

$$\text{Glucose} + \text{glucose oxidase-FAD} + H_2 \rightarrow \text{gluconic acid} + \text{glucose oxidase-FADH}_2 \qquad \text{I}$$

$$\text{glucose oxidase-FADH}_2 + 2\, CTM_{ox}{}^+ \rightarrow \text{glucose oxidase-FAD} + 2\, CTM_{red} + 2H^+ \qquad \text{II}$$

$$2\, CTM_{red} \rightarrow 2\, CTM_{ox}{}^+ + 2e^- \qquad \text{III}$$

where FAD designates the oxidized form of the flavin-adenine dinucleotide part of glucose oxidase, $FADH_2$ designates the reduced form of the flavin-adenine dinucleotide part of glucose oxidase, $CTM_{ox}$ designates the charge-transfer mediator in oxidized form and $CTM_{red}$ is the charge-transfer mediator in reduced form.

A simplified way of expressing the reactions is:

$$\text{glucose} + GOD \rightarrow \text{gluconic acid} + GOD^- \qquad \text{IV}$$

$$GOD^- + CTM_{ox}{}^+ \rightarrow GOD + CTM_{red} \qquad \text{V}$$

$$CTM_{red} \rightarrow CTM_{ox}{}^+ + e^- \qquad \text{VI}$$

The two first reactions (I, II or IV, V, respectively) take place at the interface of the liquid of the sample and the exposed surface of the sensor electrode, and the oxidation reaction of the CTM (III or VI, respectively) takes place in the electrode.

The above formalism refers to the use of a charge-transfer mediator which undergoes a one-electron redox process. However, charge-transfer mediators which undergo, e.g. a two-electron redox process may also be useful within the context of the present invention.

In theory, the system is a system wherein the glucose oxidase and the charge-transfer mediator are consumed in the process, followed by a regeneration of the parent substances in the same amounts as consumed. In principle, this should lead to a cyclically functioning system with a long period of function.

Electrodes based on the above general principle are known, but they suffer form problems caused by the depletion of the charge-transfer mediator, due to relatively high water-solubility of the oxidized form thereof.

A significant extent of depletion of the charge-transfer mediator can result in several drawbacks, e.g.

(i) only one measurement can be performed in a given sample owing to rapid loss of the charge-transfer mediator to the medium of the sample;

(ii) the reproducibility of the measurement is poor as the extent of the depletion of the charge-transfer mediator is rather unpredictable and depends on the time elapsing between exposure of the sample to the electrodes in question and the performance of the actual measurements;

(iii) the sensitivity at low glucose concentrations is very poor; and (iv) the applied potential between the sensor electrode and the reference electrode has to be rather high, leading to interference from other oxidizable substances present in the aqueous sample.

A prerequisite for a successful and reproducible measurement of the specific glucose concentration in a body fluid, in particular in whole blood, based on the above-mentioned principle using a suitable apparatus comprising the sensor electrode, a suitable reference electrode and a suitable counter electrode is thus that a sufficiently well-defined amount of the charge-transfer mediator is present throughout the measurements. Furthermore, it is advantageous if the measurement can be repeated without taking a new sample of blood and without replacing the sensor electrode.

The present invention provides such a method based on the above-mentioned electrochemical principle for measuring the glucose concentration in a sample of an aqueous medium, e.g. a sample of body fluid, such as a sample of whole blood, blood plasma, serum, urine or saliva, but the sensor electrode(s) has/have a composition and a structure which ensure that the charge-transfer mediator is present and available in an amount sufficient to ensure that the concentration of its oxidized form is maintained substantially constant during the measurement, whereby the sensor electrode(s) work(s) at a low potential in the range of 0–250 mV relative to a silver/silver chloride reference electrode operating at about 145 meq/liter chloride ion concentration (the latter concentration being of the same order as that in human plasma (about 100 meq/l)). Furthermore, the measurement can be repeated with the same sample and electrode device without any further discomfort to the patient.

It has been found that operating the sensor electrode at a relatively low potential results in a better signal-to-noise ratio and a better accuracy and reproducibility of the measurements.

Furthermore, operation of the sensor electrode at a relatively low and constant potential is very important if interference from oxidizable substances other than glucose present in the blood is to be avoided. This is explained in the following, noticing that the expression "redox potential" is intended to mean the redox potential relative to a reference electrode which is comparable to the reference electrode used according to the present invention.

Substances which have redox potentials which are lower than the redox potential of the charge-transfer mediator, e.g. 1,1′-dimethylferrocene, at which the sensor electrode is working are, if present in the sample, co-determined by the method according to the invention. To our knowledge only very few, if any, oxidizable substances which have a redox potential below the potential of 1,1′-dimethylferrocene may in general, be present in a body fluid, in particular in blood, from subjects, e.g. patients, mainly suffering from diabetes mellitus. The method of the invention has the advantage that the potential at which the electrode device operates can be kept relatively low, since the oxidation of glucose to gluconic acid is achieved enzymatically rather than electrolytically, and the reduced form of the charge-transfer mediator is present in such large amounts that (a) the percentage depletion of the reduced form due to loss of the oxidized form to the aqueous medium is very small, so that the concentration of the reduced form within the sensor electrode may be regarded as being essentially constant, and (b) the applied potential required to bring about the redox process for the $CTM/CTM^+$ is relatively low.

One way of eliminating the contribution resulting from any possible interfering substance is to use a technique which enables the contribution from any interfering substance to be subtracted from the total signal in order to give a reliable measurement of the glucose concentration.

The preferred method according to present invention is a method which is performed at a relatively low and substantially constant potential and at the same time is reproducible and has a high sensitivity. Furthermore, the method according to the invention enables the use of two different sensor electrodes (i.e. a blank sensor electrode comprising inactivated glucose oxidase (e.g. denatured by heating) and a measuring sensor electrode comprising active glucose oxidase), whereby signals resulting from interfering substances present in the aqueous sample are monitored via the blank sensor electrode and signals corresponding to the total concentration of glucose and interfering substances present in the aqueous sample are monitored via the sensor electrode comprising the active glucose oxidase. Thus, by subtracting the former signal from the latter a specific measure of the concentration of glucose in the sample can be obtained.

Until now, no such sensitive and substantially specific method for measuring the concentration of glucose in a body fluid, in particular in whole blood, has been described.

The electrode device

The electrode device according to the present invention comprises an electrode device body (also denoted an electrode body member) and the electrodes. In the following, the construction of preferred embodiments of the electrode device is described.

The electrode device body

The electrode device body may have a cylindrical rod-like shape. It is made of a slideable polymeric material. If necessary, additives may be included to obtain a polymeric material which has a sufficient hydrophilicity to ensure favorable contact between the aqueous sample and the electrode device.

The electrode body member is suitably made from a plastic material, such as a polymeric material. Such material may be of an electrically insulating or electrically conductive type. In the latter case the electrode body member may in itself function as an electrode as indicated above.

The electrode device body is suitably made of polymeric materials such as polyethylene(s), EVA, polyurethane, or polyvinylchloride(s). A preferred material is polyethylene, such as high density polyethylene or low density polyethylene, especially in admixture, the ratio between the high density and the low density polyethylene then being in the range of between 1:10 and 1:0.1, preferably in the range of between 1:5 and 1:0.5, in particular about 1:1 by weight. Suitable additives can be used to give better wetting of the surface of the electrode device, i.e. establish a better contact between the sample of the aqueous medium and the surface of the electrode device. Suitable additives are polyethylene oxide, glycerol fatty acid esters or N,N-bis(2-hydroxyethyl)dodecanamide.

The electrode device body contains at least two longitudinal channels wherein each of the electrodes are positioned. In the case of two channels, the electrodes which are placed in the channels are a sensor electrode and a combined reference and counter electrode. In the case of three channels, the electrodes are a sensor electrode, a reference electrode and a counter electrode, respectively, or two sensor electrodes (which are the same or different) and a combined reference and counter electrode. In a preferred embodiment, the electrode device body contains four channels, two of which house a sensor electrode, the sensor electrodes being the same or different, and the other two housing a reference and a counter electrode, respectively.

The channel(s) housing the sensor electrode(s), has/have substantially the same cross-sectional diameter throughout the length of the channel in order to ensure that the exposed sensing surfaces of all the electrodes remain constant from one measurement to the next. Thus, the removal of a thin slice of the electrode device before a new measurement, resulting in the exposure of a fresh surface, does not result in a change of the area(s) of the exposed surface(s) of the sensor electrode(s) included in the electrode device body. This characteristic is very important, since a variation in the area(s) of the exposed surface(s) of the sensor electrode(s) from one measurement to another leads to a corresponding, approximately linear variation in the current signal, and thus gives rise to a completely new measuring condition leading to another calibration of the system, i.e., the linear correlation between the concentration of glucose in the sample and the current generated at the sensor electrode changes its parameters (i.e. slope and intercept). By keeping the area(s) of the exposed surface(s) of the sensor electrode(s) substantially constant, i.e. the diameter of each channel is substantially constant throughout its length, the correlation between glucose and current signal is maintained substantially constant.

Electrodes

Preferably, the electrode device according to the present invention comprises a sensor electrode, a reference electrode and a counter electrode. In a preferred embodiment two sensor electrodes are present.

Sensor electrode

The preferred embodiment of a sensor electrode of the invention comprises an electrically conductive material, together with glucose oxidase and the charge-transfer mediator.

The electrically conductive material is preferably a carbon-based material such as surface-oxidized graphite particles. The size of the particles should be at most 50 $\mu$m, preferably 1-20 $\mu$m.

In a preferred embodiment, the electrically conductive material is a carbon-based paste containing a pasting material. Useful pasting materials are non-polar substances which are substantially immiscible with water, such as paraffin, paraffin oil, silicone oil etc., paraffin oil being preferred.

The amount of the non-polar pasting material present in the paste is suitably about 30–40%, preferably about 30–45% given as weight percentages based on the total weights of carbon-based, e.g. graphite-based, particles and the pasting material.

The pasting material constitutes a support and a dispersion medium for a charge-transfer mediator and regulates the release of the charge-transfer mediator in a controlled way during the measurement. Furthermore, the pasting material serves as a cohesive medium by filling the interstices between the graphite particles.

The charge-transfer mediator which is present in the sensor electrode is preferably an organometallic compound having a redox potential $E_0$ in the range of 0–150 mV, the organometallic compound preferably being very soluble in a non-polar pasting material, such as paraffin oil, and substantially insoluble in water. A preferred type of organometallic compound is a metallocene derivative, the reduced form of which is soluble in the non-polar pasting material. The metallocene derivative may suitably by a ferrocene derivative, i.e. a derivative of bis(cyclopentadienyl)iron(II), but other metallocenes or metallocene derivatives containing, e.g., nickel (as Ni(II)) or ruthenium (as Ru(II)) may also be used.

Preferred charge-transfer mediators for use according to the present invention are ferrocene derivatives, in particular 1,1'-dimethylferrocene.

Within the sensor electrode, the charge-transfer mediator is present in the reduced form (e.g. as 1,1'-dimethylferrocene). Due to the relatively non-polar nature of the charge-transfer mediator in reduced form and its low solubility in aqueous medium it is predominantly present in the non-polar pasting material, the pasting material thus functioning as a high-capacity reservoir of charge-transfer mediator.

In addition, the charge-transfer mediator may, depending on its solubility in the non-polar pasting material, also be present in the form of solid particles.

In a preferred embodiment the pasting material is paraffin oil and the charge-transfer mediator is 1,1'-dimethylferrocene, the latter being present in the paraffin oil in a concentration of about 0.01 to about 1.5M, preferably about 0.05-1.0M, in particular 0.07-0.7M, most preferred about 0.4-0.7M.

The amount of charge-transfer mediator in relation to the graphite particles is, in the case of 1,1'-dimethylferrocene as the charge-transfer mediator, in the range of 1-350 mg 1,1'-dimethylferrocene per gram GOD-containing graphite, preferably 1-100 mg 1,1'-dimethylferrocene per gram GOD-containing graphite, in particular 10-75 mg 1,1'-dimethylferrocene per gram GOD-containing graphite.

In one preferred embodiment the concentration of 1,1'-dimethylferrocene in the paraffin oil is about 0.1M, and 12.85 mg 1,1'-dimethylferrocene is present per gram GOD-containing graphite.

In one preferred embodiment the concentration of 1,1'-dimethylferrocene in the paraffin oil is about 0.5M, and 64.25 mg 1,1'-dimethylferrocene is present per gram GOD-containing graphite.

The enzyme preferred in the method according to the invention is glucose oxidase, which is an oxidoreductase enzyme of the classification EC 1.1.3.4. However, other enzymes which are oxidoreductases may be used, e.g. glucose dehydrogenase, L-amino acid oxidase or a glycolate oxidase.

The glucose oxidase preferred as enzyme in the sensor electrode is attached to the surface oxidized graphite particles and/or immobilized on the latter particles by means of a treatment involving the use of a carbodiimide reagent such as, e.g., 1-cyclohexyl-3-(2-morpholino-ethyl)carbodiimide metho-p-toluene sulfonate (N-cyclohexyl-N'-$\beta$-[(N-methylmorpholino)ethyl]carbodiimide p-toluenesulfonate salt). The glucose oxidase is present in the sensor electrode in an amount of at least about 1000 IU, such as at least about 2000 IU, more preferably at least about 4000 IU, most preferably at least about 6000 IU per gram of graphite, especially about 8000 IU per gram graphite.

An essential feature of the sensor electrode is that the glucose oxidase and the charge-transfer mediator are substantially uniformly or homogeneously distributed in the carbon-containing paste. In this way it is possible to cut off a thin, cross-sectional slice of the electrode and at the same time ensure that the correct and sufficient amount of glucose oxidase and charge-transfer mediator is present at the working surface of the electrode, the working surface of the sensor electrode being the surface which is exposed to the glucose-containing aqueous medium, such as a blood sample.

In a preferred embodiment of the sensor electrode for determination of glucose, two sensor electrodes are present in the electrode device. The two sensor electrodes can be similar or different. When the sensor electrodes are different, one electrode comprises the glucose oxidase in an active form and the other comprises the glucose oxidase in an inactive form which has been inactivated by heat denaturation at 50° C. for 24 hours.

The advantage of using two similar sensor electrodes for the measurements is that it is possible in this way to obtain two responses, one from each sensor electrode. The responses should be substantially equal if the measurement is performed correctly. Different responses from two similar electrodes is an indication of an unreliable measurement due e.g. to inadequate contact between the sample and the electrodes.

The advantage of using two different sensor electrodes, one containing the active enzyme and the other one containing the inactivated enzyme, it that it is possible in this way to obtain a blank response from the electrode containing the inactivated enzyme, whereby response from interfering substances can be subtracted from the measurement performed at the sensor electrode containing the active glucose oxidase.

In the method according to the invention, the measurement of the concentration of glucose in a sample of an aqueous medium is performed at a potential between the sensor electrode and a reference electrode in communication with the sample of the aqueous medium which is in a range which is about 0-250 mV when the reference electrode is an Ag/AgCl reference electrode working at a concentration of chloride ions of about 145 meq/l, or, when the reference electrode is different therefrom, which is in a range corresponding a range of about 0-250 mV measuring versus an Ag/AgCl reference electrode working at a concentration of chloride ions of about 145 meq/l.

If, e.g., the applied potential at the sensor electrode versus a reference electrode comprising Ag/AgCl in a 1M solution of KCl ($[Cl^-]_a$) is 160 mV, this value corresponds to an applied potential of 110 mV, when the measurement is performed with an Ag/AgCl electrode working at a concentration of chloride ions of about 145 meq/l ($[Cl^-]_b$). This relationship can be derived from the following equation corresponding to the Nernstian relationship:

$$E = E_o - (RT/nF)ln([Cl^-]_a/[Cl^-]_b)$$

By insertion of the relevant values in the equation it can be found that $$E = E_o - 50\ mV$$

showing that a change in the reference electrode from a reference electrode comprising Ag/AgCl in a 1M solution of Kcl in an agarose gel to a reference electrode comprising Ag/AgCl working at a concentration of chloride ions of 145 meq/l leads to shift in the potential from 160 mV to 110 mV.

In preferred embodiment of the method according to the invention the potential between the sensor electrode and the Ag/AgCl reference electrode working at a concentration of chloride ions of about 145 meq/l is in the range of about 0–200 mV, preferably in the range of 10–150 mV, in particular in the range of 20–120 mV, such as 30 mV, 50 mV or 110 mV.

Preparation of the sensor electrode

A preferred sensor electrode for the determination of glucose may be prepared in the following manner in which the preparation of the electrode material as well as the filling of the channel(s) of the sensor electrode in the electrode device body is performed.

The carbon particles, preferably graphite particles, are surface oxidized by heating, e.g. at 100° C. for a predetermined period in a well ventilated, continuously rotated vessel in the presence of dry atmospheric air. These surface oxidized graphite particles are activated with 1-cyclohexyl-3-(2-morpholinoethyl)carbodiimide metho-p-toluenesulfonate (N-cyclohexyl-N'-[β-N-(methylmorpholino)ethyl]carbodiimide p-toluenesulfonic salt), e.g. 42.3 mg per gram surface oxidized graphite particles. The activation is performed by mixing the graphite particles with the 1-cyclohexyl-3-(2-morpholinoethyl)carbodiimide metho-p-toluenesulfonate dissolved in an aqueous buffer solution, e.g an acetate buffer of pH of 4.76, followed by continuous stirring for e.g., about 2–4 hours at room temperature. After stirring, the mixture is washed several times (e.g. 4–7 times) with distilled water until approximately neutral pH (5–7), and the carbodiimide-activated graphite particles are dried by evaporation of the water, e.g. by forced evaporation using a fan, or under reduced pressure, at room temperature or by lophilization. Before immobilization of the glucose oxidase on the carbodiimide-activated graphite, the glucose oxidase is dissolved in an aqueous buffer having a suitable pH at which the enzyme is sufficiently stable, and containing a coupling reagent for coupling the enzyme to the carbodiimide-activated graphite, e.g. a phosphate buffer having a pH of 7.3 and containing 4% w/w glutaraldehyde (i.e. glutaric dialdehyde). The amount of buffer used is, e.g., 2 ml per gram carbodiimide-activated graphite particles and the amount of enzyme used is, e.g., at least 4000 IU, preferably 8000 IU per gram of the carbodiimide-activated graphite particles. The immobilization is performed by suspending the carbodiimide-activated graphite particles in the buffer containing the enzyme and the coupling reagent. The suspension is stirred continuously for about 16 hours at 4° C. followed by removal of the water by evaporation, e.g. at reduced pressure, at room temperature or by lyophilization. Using glutaraldehyde as coupling reagent the enzyme, preferably glucose oxidase, becomes covalently bonded to the graphite particles. However, physical adsorption of the enzyme to the surface of the particles may also be of some importance in relation to the immobilization of the enzyme on the particles.

In the following the term "GOD-containing graphite" is used to mean carbodiimide-activated graphite particles comprising the glucose oxidase, the particles being prepared in the manner described above.

The GOD-containing graphite is sieved through a 48 mesh (mesh size corresponding to a sieve having an opening of 297 μm) and the sieved material is then mixed with a sufficient amount of the non-polar pasting material, i.e. paraffin oil, in which the charge-transfer mediator, i.e. 1,1'-dimethylferrocene, has been dissolved. Preferably, the concentration of the 1,1'-dimethylferrocene solution is about 0.01–1.5M, preferably about 0.05–1.0, in particular about 0.07–0.7M, in particular about 0.01–0.7M, most preferred about 0.4–0.7M in paraffin oil. The amount of the 1,1'-dimethylferrocene in paraffin oil is larger than the required and final amount in the sensor electrode. The reason for this is that it should be possible to obtain a dispersion of GOD-containing graphite in the 1,1'-dimethylferrocene solution, the dispersion having a consistency which allows the appropriate channel(s) in the electrode device body to be filled. The excess amount of the 1,1'-dimethylferrocene solution is easily removed after filling of the channel(s) of the sensor electrode in the electrode device body by centrifugation. The amount of 1,1'-dimethylferrocene used is preferably 3–4 times greater than the amount necessary to establish a final concentration of about 10–75 mg 1,1'-dimethylferrocene per gram GOD-containing graphite in the sensor electrode, and an amount of about 2–3 ml 1,1'-dimethylferrocene solution, preferably with a concentration of about 0.07–0.7M, more preferred in a concentration of about 0.4–0.7M, is normally used per gram GOD-containing graphite.

To fill the sensor electrode channels(s), the electrode device body is placed in a special holder having a small funnel-shaped reservoir at the top. The dispersion containing the GOD-containing graphite and the 1,1'-dimethylferrocene in paraffin oil solution is then poured into the reservoir. The electrode device body equipped with the filled reservoir is then centrifuged at about 15,000–50,000×g for about 5–30 min, the centrifugation preferably being performed at about 20,000×g for about 10 min, the electrode body device being positioned in an inverted position during centrifugation (i.e. that end of the device from which slices later are removed being uppermost, the funnel-shaped reservoir being inserted in that end). By the centrifugation the air is displaced from the channels and the GOD-containing graphite particles sediment, the interstices between the particles thus being filled with the 1,1'-dimethylferrocene in paraffin oil, and the excess amount of 1,1'-dimethylferrocene in paraffin oil remaining as a supernatant in the upper part. After centrifugation the excess 1,1'-dimethylferrocene in paraffin oil is easily removed and the surface of the sensor electrode is levelled with the surface of the electrode device body by cutting off a suitable cross-sectional portion of the electrode device.

The advantages achieved by using the above-mentioned method of preparing and filling the sensor electrode channel(s) in the electrode device body is that the components of the sensor electrode(s) become packed uniformly or homogeneously in the graphite-containing paste, the interstitial spaces between the GOD-containing particles being filled with the 1,1'-dimethylferrocene in paraffin oil such that substantially no air bubbles remain within the sensor electrode(s).

Another way of filling the sensor electrode channel(s) in the electrode device body is by suitable fixation of the electrode device body and subsequent filling in vacuo; for example the sensor electrode channel(s) can be filled by compression of the GOD-containing paste into the channel(s) by use of a suitable equipment and punches to suit.

Another way of preparing the sensor electrode is to mix the GOD-containing graphite particles with a solution containing the charge-transfer mediator, preferably 1,1'-dimethylferrocene, dissolved in a mixture comprising n-pentane and the paste-forming material, e.g. paraffin oil. After intimate mixing the n-pentane is removed by evaporation and the paste is introduced into the channels in vacuo. n-Pentane can be replaced by other volatile, non-reacting organic solvents in which the charge-transfer mediator is soluble, e.g. petroleum ether.

Suitable amounts for preparation by the latter method are, e.g., about 10-15 mg 1,1'-dimethylferrocene, preferably 12.85 mg 1,1'-dimethylferrocene, 0.2-1.0 ml paraffin oil, preferably 0.6 ml paraffin oil, and 4-5 ml n-pentane per gram GOD-containing graphite.

Alternatively, suitable amounts are, e.g., about 50-75 mg 1,1'-dimethylferrocene, preferably 64.25 mg 1,1'-dimethylferrocene, 0.2-1.2 ml paraffin oil, preferably 0.6 ml paraffin oil, and 4-5 ml n-pentane per gram GOD-containing graphite.

Reference electrode

The reference electrode can be any physically suitable reference electrode of a conventional type. E.g., it can b a silver/silver chloride reference electrode or a variant thereof comprising an aqueous solution of potassium chloride (e.g. a 1M solution) in a gel (e.g. an agarose gel) and at the bottom having a silver/silver chloride electrode. In the method according to the present invention a silver/silver chloride electrode is preferred, the electrode comprising a silver wire on which a layer of silver chloride has been established by immersion in ferric chloride, or by an electrolytic treatment in 0.1M hydrochloric acid. The silver wire is rather thin, preferably having a diameter of about 100-300 $\mu$m, in particular about 200 $\mu$m. Alternatively, the reference electrode can comprise an appropriate number of silver chloride coated silver wires, each wire having a diameter of about 20-100 $\mu$m, preferably about 30 $\mu$m.

Following removal of a cross-sectional slice of the electrode device prior to performing a measurement it is clear that the freshly exposed cross-sectional surface of the silver wire is no longer covered by silver chloride. However, upon exposure to a sample of an aqueous medium which contains at least a moderate concentration of chloride ions (such as whole blood or urine) the latter cross-sectional surface rapidly becomes coated with an adequate layer of silver chloride by reaction between the silver from the silver wire and the chloride present in the aqueous sample. The chloride present in the aqueous sample may arise from dissolution of silver chloride from the periphery of the exposed silver surface of the reference electrode itself and/or from the content of chloride ion in the sample. In the case where the aqueous sample itself contains only a small concentration of chloride ions it is thus advantageous to use a reference electrode comprising a number of silver wires, whereby a greater surface area of the silver chloride from the periphery of the reference electrode surface is available to release chloride ions to the aqueous sample, resulting in the formation of the necessary layer of silver chloride on the cross-sectional surface of the silver wire.

Alternatively, the reference electrode may be made of any sliceable plastic material in which is embedded a powder comprising small silver and silver chloride particles.

The reference electrode is suitably prepared by inserting the silver wire(s) on which the silver chloride layer has been established into the reference electrode channel of the electrode device body. The silver/silver chloride electrode is then fixed into position in the channel by injecting, e.g., two-component epoxy adhesive into the free space in the channel.

Counter electrode

The counter electrode is preferably a silver wire of diameter about 100-300 $\mu$m, preferably about 200 $\mu$m (comparable to the wire use din a preferred embodiment of the reference electrode). It may also be made of any suitably electrically conductive sliceable polymer-based material, e.g. a plastic material, or an electrically conductive carbon-based paste, e.g. a graphite-based paste.

During the measurement, the counter electrode delivers an electrical current which counterbalances the current generated at the sensor electrode as a result of the electrochemical reaction at the surface exposed to the sample, and as a result a fixed, constant potential between the sensor electrode and the reference electrode can be maintained.

Theory

Operation of the sensor electrode of an electrode device according to the invention at relatively low and constant potential is very important if interference from oxidizable substances other than glucose present in the blood is to be avoided.

In addition, the measurement must be reproducible and accuracy should be high, particularly at low glucose concentrations (as would be the case, e.g., for a patient in hypoglycemic coma). The patient himself should be able to check the correct functioning of the electrode device by using a single test solution and finally it should be possible to manufacture the sensor on a large scale to strict specifications.

To understand how these conditions are fulfilled in the context of the invention, some understanding of the mechanism of operation of the electrode device of the invention, particular the sensor electrode, is necessary.

Without being limited to any specific theory, a model describing the principle involved is presented in the following:

The main points can be summarized as follows:

At the interface between the pasting material (PM) and an aqueous medium, the ratio between the concentration of the charge-transfer mediator in the pasting material and that in the aqueous medium is determined by the appropriate partition coefficient. Thus by fixing the concentration in the pasting material, the concentration in the aqueous medium is thereby well-defined at the interface.

The reduced form of the charge-transfer mediator (CTM) diffuses from the pasting material into the reaction layer in the immediate proximity of the cross-sectional surface of the sensor electrode. The flux is proportional to the gradient between the surface of the pasting material (PM) and the carbon (graphite) surface to which GOD is bound or adsorbed. The relation between the flux (F) and the gradient has the following form:

$$F = P(M_p - M_i) \qquad (1)$$

P: apparent permeability (cm.sec$^{-1}$);

$M_p$: concentration of the mediator at the PM surface, assumed constant;

$M_c$: concentration of the mediator at the carbon surface.

At the carbon (graphite) surface in the sensor electrode, CTM is oxidized to CTM$^+$. At this may be presumed to be a Nernstian exchange, the following relation should approximately apply:

$$E - E_o = RT/nF \log([CTM^+]/[CTM]) \qquad (2)$$

n=1)

(where E is the electrode potential relative to a chosen reference point and $E_o$ is the standard electrode potential relative to the same reference point) i.e.

$$[CTM^+]/[CTM] = \exp[(E-E_o)F/RT].$$

It should be recognized that the value of the potential, E, is a function of the ratio of $[CTM^+]$ to $[CTM]$ and not of the absolute concentration ($[CTM^+]$) of $CTM^+$.

Both specifies CTM and $CTM^+$ diffuse in the aqueous medium in the proximity of the sensor electrode surface in such a way that their actual concentrations in the reaction layer cannot be safely predicted.

Diffusion of both species must be compensated by the flux F. This must not exhaust the store of mediator contained in PM, and for this reason the charge-transfer mediator must be much more soluble in PM than in the aqueous medium. In the absence of glucose, the continuous production of $CTM^+$ at the graphite surface and its leakage into the surrounding aqueous medium (bulk) is responsible for part of the background diffusion current $I_d$. The remaining part of the background current is mainly due to the presence of undetermined extraneous chemicals in blood and even in GOD itself. Diffusion of the species CTM does not produce any current.

When the applied potential is progressively increased, starting from zero, the amount of $CTM^+$ increases correspondingly at the sensor electrode surface, increasing the leakage of $CTM^+$ and thus $I_d$. As the flux F increases, the concentration gradient between the PM surface and the carbon surface builds up and $M_c$ falls, and this gradient has a limiting value when $M_c$ falls to zero.

This behaviour can be calculated, and a closed-form solution can be obtained. Alternately, it can be simulated. A comparison between theory and experiment is shown in FIG. 27.

For an actual electrode, approximate values can be formed for P and $M_p$ from the maximum value of $I_d$ and from its half-wave potential, $E_{d\frac{1}{2}}$ (E at $I_d(max)/2$). These two parameters characterize this part of the sensor electrode.

In the presence of glucose, the enzyme (GOD) begins to play a role. The exact mechanism of both oxidation of glucose and of electron transfer from the reduced form of the enzyme to the charge-transfer mediator is still unknown. However, the present data can qualitatively and quantitatively be, at least partly, explained by the following kinetic relation compatible with the known stoichiometry:

The glucose velocity (v):

$$v = \frac{V_{max}}{1 + K_m/[\text{glucose}] + K_f/[CTM^+]^2} \quad (3)$$

where $V_{max}$ is an amplitude parameter (i.e. a "maximum" velocity), and $K_m$ and $K_f$ are constants.

The catalytic current due to glucose oxidation is thus characterized by the above three parameters, $V_{max}$, $K_m$ and $K_f$. Only the first of these can be experimentally manipulated. The catalytic current is superimposed on the background current, $I_d$.

FIG. 28 shows the superposition of the catalytic current and the background current, both simulated and experimentally determined.

From FIG. 28 it is clear, that the catalytic current ($I_c$) builds up above the diffusional current, in other words when the latter has already reached a plateau value. From the above, it is apparent that under these conditions the concentration of CTM at the carbon surface ($M_c$) must be very low, and the resupplying of CTM from the PM phase is solicited at "full power", i.e. maximally, because the concentration gradient $M_p - M_c$ can no longer increase to cope with rising demand, for example in the case of convection in the aqueous medium of the sensor electrode surface. It can be shown, both theoretically and experimentally, that the reproducibility and/or the signal-to-noise ratio are poor in this operational range.

In order to obtain a much better reproducibility, it is necessary to separate, along the voltage abscissa, the catalytic wave from the diffusional wave. The former must develop at a lower voltage in a range in which the diffusional current is far from being at its maximum. Fortunately, this can easily be achieved by increasing the charge-transfer mediator concentration. The $E_{d\frac{1}{2}}$ for $I_d$ is concentration independent, whereas $E_{c\frac{1}{2}}$ (E at $I_c(max)/2$), for $I_c$ moves towards lower potentials when the charge-transfer mediator concentration increases. This point is exceedingly important. The separation of $I_c$ from $I_d$ is by far the most important aspect of this aspect electrode principle. Put in another way, reliability is achieved by replacing the using regulation of $CTM^{30}$ concentration by means of potential variation by a judicious choice of the preparation of the pasting material.

This separation of $I_c$ from $I_d$ is demonstrated both experimentally and in simulation in FIG. 29.

Two important advantages of this technique are the very low background current at zero glucose concentration allowing a "single-point" calibration and leading to improved linearity (at high $[CTM^+]$), as can be expected from relation (3) and is apparent from FIG. 30.

The specifications using the present techniques are:
(with 1,1'-dimethylferrocene as CTM, and with an Ag/AgCl reference electrode operating at 145 meq/l of chloride, i.e. at a chloride concentration not substantially different from that found in normal human whole blood plasma)

| $E_{d\frac{1}{2}}$ for $I_d$ | 225 mV | upper limit | 225 + 20 mV |
|---|---|---|---|
| | | lower limit | 225 − 50 mV |
| $E_{c\frac{1}{2}}$ for $I_c$ | lower than 0 | | |

Preferred working voltage 20–100 mV, in particular 20–30 mV; operating range 20 to 200 mV The partition coefficient of 1,1'-dimethylferrocene between paraffin oil and pure water is found to be in the range of 1000–5000.

Method to ensure that the charge-transfer mediator is present in the sensor electrode in a sufficient amount The amount of the charge-transfer mediator present in the sensor electrode is a very important feature of the present invention. The amount should throughout the life time of the electrode device be sufficiently high to ensure that the concentration of the oxidized form of the charge-transfer mediator in the aqueous sample is substantially constant during the measurement.

Further to the specifications given above the sensor electrode according to the invention, the following method may be used to ensure that a sufficient amount of 1,1'-dimethylferrocene is present in the sensor electrode.

The availability of a sufficient amount of the reduced form of the charge-transfer mediator, e.g. 1,1'-dimethylferrocene can be assessed by the electrode current generated when measuring on a standardized glucose-free sample, such as, e.g., polyvinylpyrrolidone solution. The generated flow current follows a Nernstian relationship and after correction for the current of the background, the relationship is approximately $$\frac{I_x + 25 \text{ mV}}{I_x} = e$$

(where e is the base of natural logarithm) on sweeping the potential over the range of 0 to 250 mV ($0 < x \leq 225$ mV). The potential given is the potential between the sensor electrode and a suitable reference electrode such as a Ag/AgCl electrode, and further characterized in that the measurement is performed at a potential where the absolute value of the slope of a plot of the current versus potential is substantially zero and less than 0.01 $\mu$A/mV.

The invention will now be further described with reference to the drawings, wherein FIG. 1 is a perspective view of a first embodiment of the measuring apparatus according to the invention, FIGS. 2 and 3 are side views in an enlarged scale of an electrode assembly or electrode device having a cutter counter member mounted slideably thereon, FIG. 4 is a top plan view of the electrode assembly or electrode device shown in FIGS. 2 and 3, FIGS. 5 and 6 are side views and partially sectional views of the apparatus shown in FIG. 1 with the lid member in an open and closed position, respectively, FIG. 7 is a top plan view of the apparatus wherein the lid member and certain wall parts have been removed to show a ratchet mechanism, FIG. 8 is a side view illustrating an electrode assembly as shown in FIGS. 2-4 being inserted into the apparatus shown in FIGS. 5-7, FIG. 9 is a fragmentary sectional view of the apparatus shown in FIGS. 5-7 illustrating a skin puncturing mechanism of the apparatus in an enlarged scale, FIG. 10 is a side view of the apparatus illustrating how a driving spring of the skin puncturing mechanism may be tightened, FIG. 11 is a perspective view of a second embodiment of the measuring apparatus according to the invention, FIGS. 12-18 illustrates a sequence of operational steps of the apparatus during use, and FIG. 19 is the display of the measuring apparatus shown in an enlarged scale, FIG. 20 is an overall schematic and block diagrammatical view of a prototype implementation of an electronic circuitry of an apparatus according to the present invention, FIGS. 21-24 are block diagrammatical view of electronic circuities of individual sections of the prototype implementation shown in FIG. 20, FIG. 25 is a diagrammatical view of responses generated by means of a test bench apparatus illustrating the dependency of current responses generated by an apparatus according to the present invention as a function of on the one hand a polarizing voltage supplied to two electrodes of the apparatus and on the other hand the content of blood glucose in samples, FIG. 26 is a diagrammatical view of two response curves generated by two sensor electrodes constituting two components of an electrode device of the apparatus according to the present invention, FIGS. 27A and 27B are theoretical and experimental curves, respectively, of potential versus different current for various concentrations of 1,1'-dimethylferrocene, FIGS. 28A and 28B are theoretical and experimental curves, respectively, of potential versus diffusional plus catalytic current for various concentrations of glucose, FIGS. 29A and 29B are theoretical and experimental curves, respectively, of potential versus diffusional plus catalytic current for various concentrations of glucose, FIGS. 30A and 30B are theoretical and experimental curves, respectively, of potential versus diffusional plus catalytic current for various concentrations of glucose, and FIG. 30C shows calibration curves for glucose concentration in human whole blood versus integrated current at two different applied potentials.

The measuring apparatus shown in FIGS. 1 and 5-7 comprises a frame part or housing 10 and a lid-like member 11 mounted on the housing 10 so as to be rotatable in relation thereto about an axis 12 as indicated by an arrow 13 in FIG. 1. The housing 10 as well as the lid-member 11 may be made from two or more separately manufactured parts which may, for example, be made from plastics material by die casting. The housing 10 defines a cavity 14 (FIGS. 5 and 6) therein for receiving an electrode device or electrode assembly 15 as that shown in FIGS. 2-4.

The electrode assembly shown in FIGS. 2-4 comprise a cylindrical, rod-shaped electrode body member 16 having a collar-like enlargement 17 at one end. The electrode body member 16 may be made from plastics material or another electrically insulating material, and a number of mutually spaced, rod-shaped electrodes 18-20 are embedded in the electrode body member 16 and extend longitudinally through the electrode body member 16 from an end surface 21 opposite to the enlargement 17. Each of the electrodes 18-20 is connected to a terminal pin 22 (FIG. 5). The terminal pins 22, which are arranged within the collar-like enlargement 17, form an electrical connector plug. The electrodes each having a free end surface exposed at the end surface 21 of the electrode body member 16, may comprise a pair of sensor electrodes 18, a reference electrode 19, and a counter electrode 20. Each of theses rod-shaped electrodes 18-20 has a substantially uniform cross-section at least along a substantial part of the length of the electrode assembly 15 from the end surface 21.

The collar-like enlargement 17 of the electrode assembly 15 has radial projections 23 formed thereon, and an inlet opening 24 defined in the top wall of the housing 10 (FIG. 7) has a contour corresponding to the outer contour of the enlargement 17 so that the electrode assembly 15 may be inserted into the cavity 14 through the inlet 24 in the correct rotational position only. Before the electrode assembly is mounted in the cavity 14 of the housing 10, the cylindrical end portion of the electrode assembly is inserted through a circular opening defined in a cutter counter member 25 as shown in FIGS. 2-4. The counter member 25 has a pair of axially inwardly extending legs 26 having radial outer surfaces being substantially aligned with the radial outer surfaces of the projections 23 of the enlargement 17. Thus, when the electrode assembly 15 with the counter member 25 mounted thereon (FIG. 8) is inserted into the cavity 14 through the inlet opening 2 (FIG. 5), the bottom surface of the counter member 25 is positioned in engagement with the upper wall surface of the housing 10, and the end surface 21 of the electrode assembly 15 is substantially aligned with or extends slightly from the upper surface of the counter member 25. A cutting member or cutting blade 27 having a cutting edge 28 is mounted in the rotatable lid member 11 in such a position that cutting edge 28 is arranged substantially in the plane defined by the upper surface of cutter counter member 25 and that the cutting edge 28 is moved along a circular path intersecting the electrode assembly 15, when the lid member 11 is rotated as indicated by the arrow 13 in FIG. 1. This means that rotation of the lid member 11 causes that a thin slice is cut from the upper end portion of the electrode assembly 15 if such end portion extends slightly beyond the outer surface of the cutter counter member 25. In fact, the apparatus is adapted to move the electrode assembly 15 longitudinally outwardly by a small increment each time the lid member 11 is rotated 360°, so that a thin slice will be cut from the outer end of the electrode assembly for each rotation of the lid member 11 as will be described in more detail with reference to FIGS. 5-7.

As shown in FIG. 5 the lid member 11 is fastened to the outer end of a shaft 29 defining the axis of rotation 12 and having a driving gear 30 mounted on its inner end. The gear 30 is meshing with an idle gear 31 which in turn is meshing with a driven gear 32 mounted on one end of a screw spindle 33 rotatably mounted within the housing 10 and extending substantially parallel with the electrode assembly 15 inserted in the cavity 14. An electrical connector socket 34 is arranged in the cavity 14 and is aligned with the inlet opening 24 so that the terminal pins 22 of the electrode assembly are received in the socket 34 when the electrode assembly 15 is inserted into the cavity 14 as described above. This means that the electrodes 18-20 of FIG. 4 are electrically connected to an electronic measuring circuitry arranged within the housing 10 as diagrammatically indicated in FIG. 6. Such measuring circuitry may comprise a visual display 36 (FIG. 8).

The socket 34 is connected to a screw engaging member 37 through a flexible U-shaped connecting part 38. The screw engaging member has a concave threaded surface part 39 forming part of a cylinder surface and being biassed into engagement with the outer threads of the screw spindle 33 by the connecting member 38.

Rotation of the lid member 11 also causes rotation of the driving gear 30, whereby the screw spindle 33 is rotated via the gears 31 and 32. The thread engagement between the screw spindle 33 and the screw engaging member 37 causes displacement of the engaging member 37 and of the socket member 34 and consequently of the electrode assembly 15 in its longitudinal direction, when the screw spindle 33 is caused to rotate by rotating the lid member 11. A pawl 40 (FIG. 7) may engage with one of the gears 30-32 so as to form a ratchet mechanism permitting rotation of the lid member 11 in only one direction, namely in the direction causing an upward movement of the socket 34. The gear ratio may be chosen so that the slice cut from the free end of the electrode device 15 has a desired thickness. In the presently preferred embodiment the gear ratio is chosen so that one rotation of the lid member 11 causes an upward movement of the electrode assembly 15 by an increment corresponding to half the pitch of the screw thread of the screw spindle 33. Thus, the increment or the slice thickness may, for example, be 0.2-0.4 mm, preferably 0.3 mm.

The lower end of the screw spindle 33 may be journalled in a bearing block 41, and the bottom surface of a cam disc 42, which is fastened to the screw spindle 33, is in engagement with an adjacent upper cam surface of the bearing block. The cooperating cam surfaces are shaped so as to move the screw spindle 33 and consequently the socket 34 and the electrode assembly 15 slightly axially between an extended position in which the upper end surface 21 of the electrode assembly 15 extends slightly above the upper outer surface of the counter member 25, and a retracted position in which the end surface 21 of the electrode assembly 15 is slightly retracted, for example about 1 mm in relation to the outer surface of the counter member 25 (FIGS. 2 and 3) so that the end surface 21 forms the bottom of an upwardly open, cup-shaped cavity or measuring chamber 21a as shown in FIG. 5. The interengaging cam surfaces are shaped so that the end portion of the electrode assembly 15 is retracted when the lid member 11 is in its open position as shown in FIGS. 5, 8 and 14-17, and in its extended position when the cutting edge 28 of the cutting blade 27 passes the electrode assembly 15.

As will be described in more detail below the lid member 11 is rotated so as to cut a thin slice from the free upper end portion of the electrode assembly 15 before exposing the end surface 21 of the electrode assembly to a liquid sample to be measured. This means that the electrode assembly 15 is eventually consumed so that it must be replaced when a number of measurements have been made and the socket 34 has been moved to an upper position within the cavity 14 of the housing as shown in FIG. 6. In this position the free, hook-shaped ends of the legs 26 of the counter member 25 (FIGS. 2 and 3) are engaging behind the enlargement 17 of the electrode assembly 15 so that the remaining part of the electrode assembly 15 may be removed from the cavity 14 in the housing 10 by removing the cutter counter member 25 from the upper wall of the housing. Before a new electrode assembly 15 may be inserted in the cavity 14 the socket 34 and the screw engaging member 37 connected thereto by the connecting part 38 must be returned to its lower position. One end of a string member 43, such as a fishing line or cord, is connected to the engaging member 37 or the connecting part 38, and the other end portion of the string member 43 is wound on a winding member 44 which is rotatably mounted on the inner surface of the bottom wall of the housing 10. The winding member 44 is connected to a screw member 45, which extends through the bottom wall of the housing 10 and is provided with an outer slot shaped so that the winding member may be rotated in one direction only, for example by means of a coin. When the winding member is rotated in said direction, the string member 43 is wound unto the winding member, whereby the string member is tensioned so as to apply a downwardly directed force to the screw engaging member 37. Because the space defined between the socket 34 and the engaging member 37 is no longer occupied by the enlargement 17 of the electrode assembly 15, the screw engaging member 37 may flex out of engagement with the screw threads of the spindle 33 so that the socket 34 and the engaging member 37 may be moved downwardly to the lower position shown in FIG. 5. Now, a new electrode assembly 15 may be mounted in the cavity 14 of the housing 10 in the manner described above.

As described more detailed below the measuring apparatus may be used for measuring a constituent or a small liquid sample which may be arranged in the cup shaped measuring chamber defined by the end surface 21 of the electrode assembly 15 and by the surrounding wall parts of the cutter counter member 25 (FIGS. 2 and 3). The liquid samples to be measured may be body liquids or liquids of any other type. However, the preferred embodiment of the apparatus is adapted to measure a constituent of a blood sample. Thus, the apparatus may be used by diabetics for determining the content of glucose in a blood sample, which may be a single drop of blood. Therefore, the apparatus comprises a skin puncturing mechanism 46 for puncturing the skin of the user so as to collect a drop of blood from the puncture. This skin puncturing mechanism is shown in FIG. 9. A skin puncturing needle 47 is mounted at the free end of a flexible arm 48 within a needle chamber 49. The pointed end of the needle is arranged within the chamber 49 opposite to an opening 50 formed in the bottom wall of the housing 10. An impact pin 51 aligned with the needle 47 is mounted so as to be axially displaceable under the influence of a strong compression spring 52 surrounding the upper end portion of the pin 51 and a weaker compression spring 53 surrounding the lower end of the pin 51. An upper hook-shaped end 54 of the pin may engage with a depressible button 55 mounted in a housing wall part 56. In this engaging position, which is shown in FIG. 9, the strong compression spring 52 having its ends in engagement with the depressible button 55 and an enlargement 57 of the impact pin 51, respectively, is fully tightened, while the weaker compression spring 53 biassing the pin 51 in the opposite direction, is released. The enlargement 57 of the pin cooperates with a cut-out 58 in a bracket 59 of plate metal fastened to the housing 10, so as to limit the downward movement of the impact pin 51.

When the pin 51 is in the position shown in FIG. 9, the user may place the tip of his finger so as to cover the opening 50 in the bottom wall of the housing 10. Thereafter, the button 55 is depressed and brought out of engagement with the hook shaped end 54. Now, the impact pin 51 is suddenly moved downwardly under the influence of the spring bias of the compression spring 52. When the lower end surface of the pin 51 hits the upper end of the needle 47, the flexible arm 48 is bent so that the pointed end of the needle is moved outwardly through the opening 50, whereby the skin of the finger tip is punctured by the needle, and a drop of blood to be measured may be collected from the puncture. When the skin puncturing mechanism 46 has been fired, the wall part 56 and the depressible button 55 mounted therein are displaced downwardly as illustrated in FIG. 10. The downward movement of the button 55 in relation to the pin 51 causes tightening of the compression spring 52 and re-engagement of the hook shaped end with the button 55. When the displaceable wall part 56 is moved back from the position shown in FIG. 10 to its starting position, the mechanism 46 is ready for further use. The downward movement of the displaceable wall part 56 may cause activation of a micro switch 60 which may send a signal to the electronic measuring circuitry, so that the measurement result of the last measuring may be shown on the display 36 (FIG. 11). The electronic circuitry 35 may be powered by a battery (not shown) arranged in a battery chamber 61 formed in the housing 10, FIG. 10.

It should be understood that an outer end section or slice may be removed or cut from the electrode assembly 15 in any suitable manner before a measurement is made. FIG. 11 shows a modified embodiment of the measuring apparatus, wherein the lid-like member 11 is reciprocatingly movable in relation to the housing 10 rather than rotatable. Also in this case a mechanism for incrementally moving the electrode assembly 15 axially outwardly for each reciprocating movement of the lid member 11 should be provided. In the embodiment shown in FIG. 11 the battery chamber may be defined in the bottom part of the housing 10, and access to the battery chamber may be obtained by removing a hood-shaped bottom part 62 of the housing. Otherwise, the apparatus shown in FIG. 11 may function similar to the apparatus described with reference to FIGS. 1-10.

The use of the apparatus illustrated in FIGS. 1 and 5-10 will now be described with reference to FIGS. 12-18. As mentioned above, the electrode assembly 15 is being consumed during use of the apparatus because a thin slice is cut from the free end of the electrode assembly for each measurement. When the electrode assembly has been consumed, for example after about 100 measurements, or if the display 36 of the apparatus indicates that the electrode assembly should be replaced, for example because it has been destroyed by a too high or too low storing temperature, the electrode assembly 15 is replaced by a new one as described above. Preferably, the cutting blade 27 is also replaceably mounted, and the cutting blade 27 may then also be replaced. The electrode assembly 15 or the cutter counter member 25 mounted thereon may contain coded information for calibrating the electronic measuring circuitry 35 of the apparatus to the type of the new electrode assembly 15. The apparatus may now be stored in the condition illustrated in FIG. 12, where the lid member 11 is in its fully closed position in which the exposed end surface 21 of the electrode device or electrode assembly 15 is protected. The apparatus may now be carried by the user in pocket or a hand bag.

When a measurement is to be made, the lid-member 11 is moved axially outwardly to a position shown in FIG. 13 so as to move a lower skirt part of the lid member 11 out of engagement with a block shaped portion 63 extending upwardly from the top wall of the housing 10. The lid is now rotated 180° from the position shown in FIG. 13 to the position shown in FIG. 14, whereby the cutting edge 28 of the cutting blade 27 mounted in the lid member 11 intersects the upper free end portion of the electrode assembly 15 so that a thin slice having a thickness of for example 0.2-0.4 mm or about 0.3 mm is cut from the electrode assembly so that a fresh, non-contaminated exposed end surface 21 is provided. The rotating movement of the lid member 11 also causes that the electronic measuring circuitry 35 is energized and a visual indication appears on the display 36, FIG. 19. The display may indicate the waiting time in seconds as shown in FIG. 15. If the apparatus has registered an excessively high or excessively low storing temperature, for example a temperature above 40° C. or below 0° C., since mounting of the electrode assembly 15 in the apparatus, a warning sign may appear on the display, for example by lightening a symbol 64, (FIG. 19), and/or by a flashing symbol 65, and a new electrode assembly 15 must be mounted in the apparatus before a measurement can be made. In case the apparatus determines that the actual temperature is within an unacceptable range, for example between 0° and 15° C. or between 35° and 40° C., this may be indicated by lightening of the symbol 65 on the display, and the measurement must be postponed till the actual temperature is within an acceptable range, for example between 15° and 35° C. If the voltage of the power source of battery of the apparatus is below an acceptable minimum limit, this may be indicated by a flashing symbol 66 on the display 36. In that case the battery must be replaced before a measurement can be made. If only the symbol 64 is lit, this may indicate that the remaining length of the rod-shaped electrode assembly 15 is below a certain limit, for example that the electrode length left is sufficient for less that ten measurements. If the electrode assembly 15 is completely consumed, the symbol 64 may be flashing, and a new electrode assembly must be mounted.

Provided that the display 36 indicates that the measuring conditions are satisfactory by lighting of the symbol 68 the user may puncture the skin on a finger tip by means of the skin puncturing mechanism 46 in a manner described above so as to provide a drop of blood. As described previously, after cutting the electrode assembly the fresh end surface 21 of the assembly may be slightly retracted, for example about 1 mm, in relation to the outer surface of the cutter counter member 25 so as to provide a small cup-shaped measuring chamber having a bottom formed by the end surface 21. The drop of blood 67 (25-50 $\mu$l) may now be introduced into the measuring chamber as shown in FIGS. 15 and 16 so that the end surface 21 of the electrode assembly 15 is covered thereby. In case the blood does not sufficiently cover the exposed end surfaces of all of the electrodes 18-20 this may be indicated by flashing of a symbol 68 of the display 36, and more blood must be supplied to the measuring chamber or the measurement procedure must be restarted. If the end surface 21 is sufficiently covered by blood, the symbol 68 is extinguished, and a countdown of the waiting time indication of the display 36 is initiated. When the waiting time indication has been counted down to zero, the waiting time indication is extinguished on the display and is replaced by an indication of the measuring result, for example the concentration of the constituent, such as glucose, being measured. In FIG. 17 the display 36 indicates that the glucose concentration in the drop of blood 67 is 12.6 mmol/l. When the measurement has been completed, the blood is removed from the measuring chamber, and the lid member 11 may be moved back to its closed starting position as shown in FIG. 18. The indication of the measuring result may remain at the display 36 for a certain predetermined period of time, for example five minutes. When a new measurement is to be made, the procedure described above is repeated, and before a new drop of blood is introduced into the measuring chamber a thin slice is cut from the free end portion of the electrode assembly 15 so as to provide fresh, uncontaminated electrode surfaces before the new liquid sample is introduced into the measuring chamber.

In FIG. 20 a block diagram of a prototype implementation of an electronic circuitry of the apparatus according to the present invention is shown. The electronic circuitry comprises a total of seven blocks designated B1, B2, B3, B4A, B4B, B4C, and B4D. The electronic circuitry is, as is evident from the above description of the method according to the present invention, connected to a total of four electrodes designated S1, S2, S3 and S4 of an electrode device. The electrodes S1, S2, S3 and S4 constitute a first measuring or sensor electrode, a current or counter electrode constituted by a silver rod, a second measuring or sensor electrode, and a reference electrode constituted by a chlorinated silver rod, respectively. The electrodes S1-S4 are, as is evident from FIG. 20, connected to the block B1, which constitutes an analog amplifying and impedance transforming section, which is shown in greater detail in FIG. 21, and which is connected through lines B, C, and G to the block B4A and the block B2, respectively. The block B2 constitutes a reference voltage generator block, which is shown in greater detail in FIG. 21, and which is further connected through lines D, E and F to the blocks B4A and B3, respectively. The block B3 is shown in greater detail in FIG. 24 and constitutes a temperature sensor section, which is further connected to the block B4A through a line A for supplying a temperature measuring signal to the block B4A. The block B4A is shown in greater detail in FIG. 24 together with the blocks B4B, B4C, and B4D and constitutes a central microprocessor controlling the overall operation of the apparatus. The block B4B constitutes a display section comprising a liquid crystal display, on which information is displayed to a person operating the apparatus. The block B4C constitutes a block into which data may be input through lines P11 and P12, which data may constitute additional data relevant to the operation of the apparatus, e.g. data representing parameters or characteristics of the components or materials of the electrodes S1-S4. The block B4D constitutes an audio or signalling driver block, which is connected to an audio signalling device, such as a loudspeaker or a buzzer $X_2$. The blocks B4B, B4C and B4D are connected to the central microprocessor block B4A exclusively, as is evident from FIGS. 20 and 24.

In FIG 21 a detailed block diagram of the block B1 is shown. The block B1 comprises a total of four operational amplifiers IC4A, IC4B, IC5A and IC5B. The operational amplifiers IC5A and IC5B constitute current voltage converters, which convert current signals generated by the sensor electrodes S1 and S3, respectively, into voltage signals supplied to the microprocessor block B4A through the lines B and C, respectively. The current voltage converters are constituted by inverters. Thus, the sensor electrodes S1 and S3 are connected to the inverting inputs of the operational amplifiers IC5A and IC5B, respectively. The non-inverting inputs of the operational amplifiers IC5A and IC5B are grounded. The output of the operational amplifier IC5A is connected to the inverting input of the operational amplifier IC5A through a feed-back resistor R10 and a capacitor C3. Similarly, the output of the operational amplifier IC5B is connected to the inverting input of the operational amplifier IC5B through a feed-back resistor R11 and a capacitor C4. The capacitors C3 and C4 serve the purpose of limiting the high-frequency gain of the operational amplifiers IC5A and IC5B. The output of the operational amplifier IC5A is connected to the line B through a low pass filter constituted by a resistor R12 and a capacitor C5. Similarly, the output of the operational amplifier IC5B is connected to the line C through a low pass filter constituted by a resistor R13 and a capacitor C6.

The block B1 comprising the operational amplifiers IC4A and IC4B further receives a reference voltage signal through the line G from the block B2, which voltage reference signal is input to the non-inverting input of the operational amplifier IC4A the output of which is connected to the current or counter electrode S2. The reference electrode S4 is connected to the non-inverting input of the operational amplifier IC4B which constitutes a unity gain voltage follower, as the output of the operational amplifier IC4B is connected to the inverting input of the operational amplifier IC4B through a short circuiting connection. The output of the unity gain voltage follower constituted by the operational amplifier IC4B is connected to the inverting input of the operational amplifier IC4A, which constitutes a high-gain differential amplifier. The operational amplifier IC4A serves the purpose of clamping the potential of the current or counter electrode S2 to a potential defined by the reference voltage signal supplied to the operational amplifier IC4A through the line G and further generating an output voltage signal in response to any voltage difference between the non-inverting input and the inverting input of the operational amplifier IC4A, which output voltage signal results in that current is supplied to the current or counter electrode S2. The reference voltage signal supplied to the non-inverting input of the operational amplifier IC4A through the line G is of the order of $-110$ mV. The current signals generated by the measuring or sensor electrodes S1 and S3 are within the range of 0–15 $\mu$A, and the voltage signals generated by the current voltage converters IC5A and IC5B are within the range of 0–2.5 V in response to a current signal of the above range of 0–15 $\mu$A.

The reference voltage block B2 shown in greater detail in FIG. 22 comprises a voltage inverter circuit including an integrated electronic circuit IC1, which receives a positive supply voltage VCC at its terminal No. 8 and generates a negative supply voltage VEE at its terminal No. 5. The negative supply voltage VEE arises by charging of a capacitor C2 by discharging a capacitor C1 which originally is charged directly by the supply voltage. The positive and negative supply voltages VCC and VEE, respectively, are supplied to the active components of the electronic circuit, such as the above described operational amplifiers and the operational amplifiers to the described below.

The block B2 further comprises two operational amplifiers IC3A and IC3B which are connected in a cascade. The operational amplifier IC3A receives a positive reference voltage at its non-inverting input, which positive reference voltage is generated from the positive supply voltage VCC by means of a voltage reference circuit IC2, to which current is supplied through a resistor R1 from the positive supply voltage VCC. The reference voltage generated by the integrated circuit IC2 is output to the line F. The operational amplifier IC3A constitutes a high gain non-inverting circuit, the output of which is connected to the inverting input of the operational amplifier IC3A through a feed-back resistor R2. The inverting input of the operational amplifier IC3A is grounded through a series configuration of a resistor R3 and a variable resistor R4 by means of which the gain of the operational amplifier IC3A may be set. The output of the operational amplifier IC3A is connected to the line D and further to the inverting input of the operational amplifier IC3B through a series configuration of two resistors R5 and R6. The node of the resistors R5 and R6 is connected to the collector of an NPN transistor T1, the emitter of which is grounded, and the base of which is connected to the line E through a resistor R8. By turning on the transistor T1, the node of the resistors R5 and R6 is grounded consequently grounding the inverting input of the operational amplifier IC3B. The non-inverting input of the operational amplifier IC3B is grounded, and the output of the operational amplifier IC3B is connected to the line G and further to the inverting input of the operational amplifier IC3B through a variable resistor R7, by means of which the gain of the operational amplifier IC3B may be set. The inverting operational amplifier IC3B generates a negative reference voltage at the line G from the positive reference voltage initially generated by the integrated circuit IC32 and amplified by the non-inverting operational amplifier IC3A. By grounding the node of the resistors R5 and R6 bridging the output of the operational amplifier IC3A and the inverting input of the operational amplifier IC3B, the negative reference voltage generated by the operational amplifier IC3B at the line G may be eliminated as the line G is shifted to ground potential when the node of the resistors R5 and R6 is grounded as the transistor T1 is turned on.

The block B3 shown in greater detail in FIG. 23 constitutes, as indicated above, a temperature sensor section including a temperature sensor constituted by an integrated electronic circuit IC6, which is arranged juxtaposed the electrode device body of the electrode device described above and which is connected to the positive supply voltage VCC and to ground. The integrated circuit IC6 generates at its output a DC-signal, which corresponds to the temperature detected by the integrated circuit. The output of the integrated circuit IC6 is connected to a non-inverting input of an operational amplifier IC7A through a resistor R15, which resistor R15 further constitutes a component of a voltage divider branch further comprising a resistor R14 and a resistor R17, which voltage divider branch interconnects the positive supply voltage VCC and ground for offsetting the output of the integrated circuit IC6 and the input of the operational amplifier IC7A at a positive offset voltage determined by the resistors of the voltage divider branch.

The output of the operational amplifier IC7A is connected to the inverting input thereof through a series configuration of a variable resistor R18 and a fixed resistor R19 and further a capacitor C7, which reduces the high-frequency gain of the operational amplifier IC7A. The inverting input of the operational amplifier IC7A is connected to the line F through a resistor R16 for receiving the reference voltage generated by the integrated circuit IC2 shown in FIG. 22. The operational amplifier IC7A generates at its output a voltage signal originating from the temperature representing signal generated by the integrated circuit IC6. The output of operational amplifier IC7A is connected to a non-inverting input of a second operational amplifier IC7B, which constitutes a high gain non-inverting amplifier circuit and has its output connected to its inverting input through a resistor R22, which inverting input is grounded through a series configuration of a variable resistor R20 and a fixed resistor R2. The output of the operational amplifier IC7B is further connected to the line A for presenting a voltage signal representing the temperature detected by the integrated electronic circuit IC6 to the microprocessor of the block B4A.

In FIG. 24, the blocks B4A, B4B, B4C and B4D are shown in greater detail. Within the block B4A an integrated circuit IC8 constituting a central control means implemented by a microprocessor is included. The microprocessor IC8 receives at respective inputs the temperature signal from the block B3 through the line A, the measuring signals from the block B1 through the lines B and C, the reference voltage from the output of the operational amplifier IC3A of the block B2 through the line D, and outputs a control signal through the line E from a respective output. The microprocessor IC8 includes an internal 8-bit analog/digital converter, in which the measuring signals received through the lines B and C are converted from analog form into digital form and compared to one another so as to determine whether the measuring signals differ from the one another, and if so, whether the difference is beyond a preset acceptable threshold. The microprocessor also converts the temperature signal into digital form for calculating—in accordance with an integration routine to be described in greater detail below—a measuring signal on the basis of the measuring signals input to the microprocessor IC8 through the lines B and C and the temperature signal input through the line A. The microprocessor IC8 is further connected to an oscillator crystal X1 through respective terminals, which are further grounded through capacitors C8 and C9. Two resistors R23 and R24 serve as a voltage divider, so that the supply voltage can be monitored via the 8-bit analog digital converter. The microprocessor IC8 is further grounded through a respective terminal and generates at respective outputs display driver signals, which are supplied to the block B4B, which includes a liquid crystal display designated LCD.

The block B4C shown in the lower left-hand part of FIG. 24 includes a storage IC9 constituted by an $E^2$-PROM (Electrically Erasable Programmable Read Only Memory), which is connected to respective inputs of the microprocessor IC8 of the block B4A and further connected to the lines P11 and P12 for receiving data from an external data input source. In the prototype implementation, the data input lines P11 and P12 were used for inputting data to the $E^2$PROM IC9 representing characteristics of the electrodes of the electrode device for calibration of the measuring routine carried out within the microprocessor IC8 in calculating the measuring result on the basis of the measuring signals supplied to the microprocessor IC8 from the measuring or sensor electrodes of the electrode device through the block B1 and further the temperature signal supplied to the microprocessor IC8 from the block B3.

In the lower right-hand part of FIG. 24, the block B4D is shown including a buzzer constituting the loudspeaker $X_2$ shown in FIG. 20, which buzzer is connected to a switching transistor T2, the base of which is connected to a control terminal of the microprocessor IC8, the emitter of which is grounded, and the collector of which is connected to a first terminal of the buzzer and through and inductor L1 to the positive supply voltage VCC. The second terminal of the buzzer is grounded.

In FIG. 25 a diagram is shown comprising three response curves, which represent the current responses generated by a sensor or measuring electrode of an electrode device according to the present invention as a function of the polarizing voltage of the reference electrode relative to the current or counter electrode, i.e. the reference voltage supplied to the current or counter electrode and further as a function of the content of glucose in a blood sample as expressed in mg/dl. From FIG. 25 it is evident that a polarizing voltage of approximately 100-150 mV is an optimum polarizing voltage, as the response curves are substantially horizontal in this range due to the 0.1M 1,1'-dimethylferrocene concentration in the paraffin oil of the sensor electrodes employed in FIG. 25. Thus, any current measuring result unambiguously represents a specific blood glucose content irrespective of any variation of the polarizing voltage.

In FIG. 26, two response curves of two measuring or sensor electrodes of an electrode device according to the present invention are shown. FIG. 26 further illustrates the measuring routine carried out by the microprocessor of the electronic circuitry. For a period of time of 10 sec, after a blood sample is arranged on the exposed outer end surface of the electrode device, the electrode system is allowed to reach an equilibrium during which period of time the blood sample further reaches the temperature of the electrode device. After 10 sec, the counter or current electrode is activated and generates a polarizing voltage relative to the reference electrode resulting in that a current peak is generated. By the polarization of the test sample, a current is generated which decays as is indicated by the curves F and G. After 30 sec, the microprocessor starts integrating the areas below the curves F and G, which areas represent the charges transferred to the measuring electrodes in accordance with the equation $\Sigma I \times \Delta t = Q$ and calculates the average charge transferred to the measuring electrodes. During the measuring period, the microprocessor continuously checks whether the responses generated by the measuring electrodes differ from one another. In case a difference between the responses exceeds a predetermined threshold, the microprocessor decides that the measurement is an erroneous measurement and informs the operator thereof on the display and further through an audible alarm generated by the buzzer $X_2$.

It is believed that the measuring period and the integration period which as shown in FIG. 25 are 60 sec and 30 sec, respectively, in the prototype implementation described above may be reduced to e.g. 30 sec and 15 esc, respectively, by increasing the content of 1,1'-dimethylferrocene. By reducing the measuring period, the time during which the sample is allowed to reach the temperature of the electrode device is obviously also reduced. However, by adapting the measuring routine performed by the microprocessor to carry out an estimation of the decay of the temperature signal on the basis of the variation of the temperature signal detected by the temperature sensor, it is believed that any discrepancy between the temperature detected by the temperature sensor and the temperature of the blood sample may be compensated for.

FIG. 27.

A. The theoretical curves of potential (mV) versus the background (diffusional) current, Id ($\mu$A).

The curves show:
a: 0.0125M, 1,1'-dimethylferrocene in paraffin oil
b: 0.025M, 1,1'-dimethylferrocene in paraffin oil
c: 0.05M, 1,1'-dimethylferrocene in paraffin oil
d: 0.1M 1,1'-dimethylferrocene in paraffin oil B. The experimental curves of potential (mV) versus $I_d$ ($\mu$A).

The experimental conditions were:
temperature: 23° C.
test medium: phosphate buffer (pH 7.3) with polyvinylpyrrolidone 4.5%
electrodes: 4 electrodes embedded in a plastic rod (length=50 mm).

2 sensor electrodes diameter 2.5 mm
1 reference electrode diameter 1.5 mm
1 counter electrode diameter 1.5 mm
sensor electrodes: columns of graphite paste ended by stainless steel plugs. Paste composition: enzyme (6000 IU glucose oxidase/g of carbodiimide-activated graphite particles) covalently linked as described in Example 3 paraffin oil as pasting material (PM) charge-transfer mediator: 1,1'-dimethylferrocene dissolved in PM.

The curves show:
a: 0.01M, 1,1'-dimethylferrocene in paraffin oil
b: 0.05M, 1,1'-dimethylferrocene in paraffin oil
c: 0.01M, 1,1'-dimethylferrocene in paraffin oil
reference electrode: column of agarose gel, KCl 1M ended by a silver/silver chloride plug
counter electrode: column of agarose gel, KCl 1M ended by stainless steel plug From FIG. 27A, it is clear that the $E_{d\frac{1}{2}}$ for the background (diffusional) current is independent of the concentration of the 1,1'-dimethylferrocene solution in paraffin oil presence in the sensor electrode. The $E_{d\frac{1}{2}}$ for Id is approximately 225 mV.

FIG. 28.

A. The theoretical curves of potential (mV) versus background (diffusional) and catalytic current, i.e. $I_d + I_c$ ($\mu$A). The curves simulate different concentrations of glucose:
a: 0
b: 0.25 $K_m$
c: 0.50 $K_m$
d: 0.75 $K_m$
e: 1.00 $K_m$
f: 1.25 $K_m$
where $K_m$ is the Michaelis-Menten constant for the reaction of glucose with glucose oxidase.

B. The experimental curves of potential (mV) versus $I_d + I_c$ ($\mu$A). The experimental conditions were:
temperature 23° C.
test medium:
curve a: phosphate buffer (pH 7.3) with polyvinylpyrrolidone 4.5%
curve b: human whole blood (89 mg/dl of glucose)
curve c: human whole blood (245 mg/dl of glucose)
electrodes: 4 electrodes embedded in a 50/50 low density/high density polyethylene rod (length=50 mm).
2 sensor electrodes, diameter 2.5 mm
1 reference electrode, diameter 1.5 mm
1 counter electrode, diameter 1.5 mm
working electrodes: columns of paste ended by stainless steel plugs. Paste composition:
enzyme (6000 IU/g of carbodiimide-activated graphite particles) covalently linked as described in Example 3 paraffin oil as pasting material (PM)
charge-transfer mediator: 1,1'-dimethylferrocene $4 \times 10^{-3}$M dissolved in PM.
reference electrode: column of agarose gel, KCl 1M ended by a silver/silver chloride plug
counter electrode: column of agarose gel, KCl 1M ended by stainless steel plug From FIG. 28A and 28B it is clear that $E_\frac{1}{2}$ for ($I_d + I_c$) shifts to approximately 120 mV in the presence of glucose and when the concentration of 1,1'-dimethylferrocene is relatively low corresponding to $4 \times 10^{-3}$M.

FIG. 29

A. The theoretical curves of potential (mV) versus $I_d + I_c$ ($\mu$A). The curves simulate different concentrations of glucose:
a: 0
b: 0.25 $K_m$
c: 0.50 $K_m$
d: 0.75 $K_m$
e: 1.00 $K_m$
f: 1.25 $K_m$
g: 1.50 $K_m$
h: 1.75 $K_m$ B. The experimental curves of potential (mV) versus $I_d + I_c$ ($\mu$A). The experimental conditions are:
temperature 23° C.
test medium:
curve a: phosphate buffer (pH 7.3) with polyvinylpyrrolidone 4.5% and 145 meq/l of NaCl
curve b: human whole blood (90 mg/dl of glucose)
curve c: human whole blood (210 mg/dl of glucose)
curve d: human whole blood (347 mg/dl of glucose)
curve e: human whole blood (466 mg/dl of glucose)
electrodes: 4 electrodes embedded in a 50/50 low density/high density polyethylene rod (length=50 mm).
2 sensor electrodes, diameter 2.5 mm
1 reference electrode, diameter 1.5 mm
1 counter electrode, diameter 1.5 mm
working electrodes: columns of paste ended by stainless steel plugs. Paste composition: enzyme (8000 IU/g of carbodiimide-activated graphite particles) covalently linked as described in Example 3 paraffin oil as pasting material (PM) charge-transfer mediator: 1,1'-dimethylferrocene 0.1M dissolved in PM.
reference electrode: silver wire (diameter 100 $\mu$m) coated with silver chloride and fixed in position with polyurethane glue
counter electrode: silver wire (diameter 100 $\mu$m) in position with polyurethane glue.

From FIG. 29A it is clear that $E_\frac{1}{2}$ for the ($I_d + I_c$) is shifted to about 50 mV due to the higher concentration of 1,1'-dimethylferrocene present in the sensor electrode.

From FIG. 29A it is seen that the operational plateau values are found for potentials of about 100–110 mV when the concentration of 1,1'-dimethylferrocene is about 0.1M in paraffin oil.

FIG. 30

A. Theoretical curves of potential (mV) versus $I_d + I_c$ ($\mu$A). The curves simulate different concentrations of glucose:
a: 0
b: 0.25 $K_m$
c: 0.50 $K_m$
d: 0.75 $K_m$
e: 1.00 $K_m$
f: 1.25 $K_m$
g: 1.50 $K_m$
h: 1.75 $K_m$ B. The experimental curves of potential (mV) versus $I_d+I_c$ (μA). The experimental conditions are the same as given in FIG. 29B but the concentration of 1,1'-dimethylferrocene in paraffin oil was 0.5M.

FIG. 30

C. Calibration curves for the glucose concentration in human whole blood versus the integrated current $(I_d+I_c)$ (μA sec). The upper curve is obtained using an applied potential of 110 mV, and the lower curve is obtained using an applied potential of 30 mV. The sensor electrode comprises 0.5M 1,1'-dimethylferrocene in paraffin oil, and the reference electrode is an Ag/AgCl electrode working at 145 mEq/l of chloride ions.

FIG. 30A shows that $E_i$ for $I_d+I_c$ shifts to about zero or below zero, the concentration of 1,1'-dimethylferrocene in paraffin oil being 0.5M in the sensor electrode. This point is extremely important since a prequisite for working at a low potential between the sensor electrode and the reference electrode is that the contribution to the generated current from $I_c$ is very small. To achieve a zero contribution or only a small contribution from $I_d$, the $E_i$ for the Id should ideally be zero or below zero.

EXAMPLES

EXAMPLE 1

Figures 1, 2, 3:
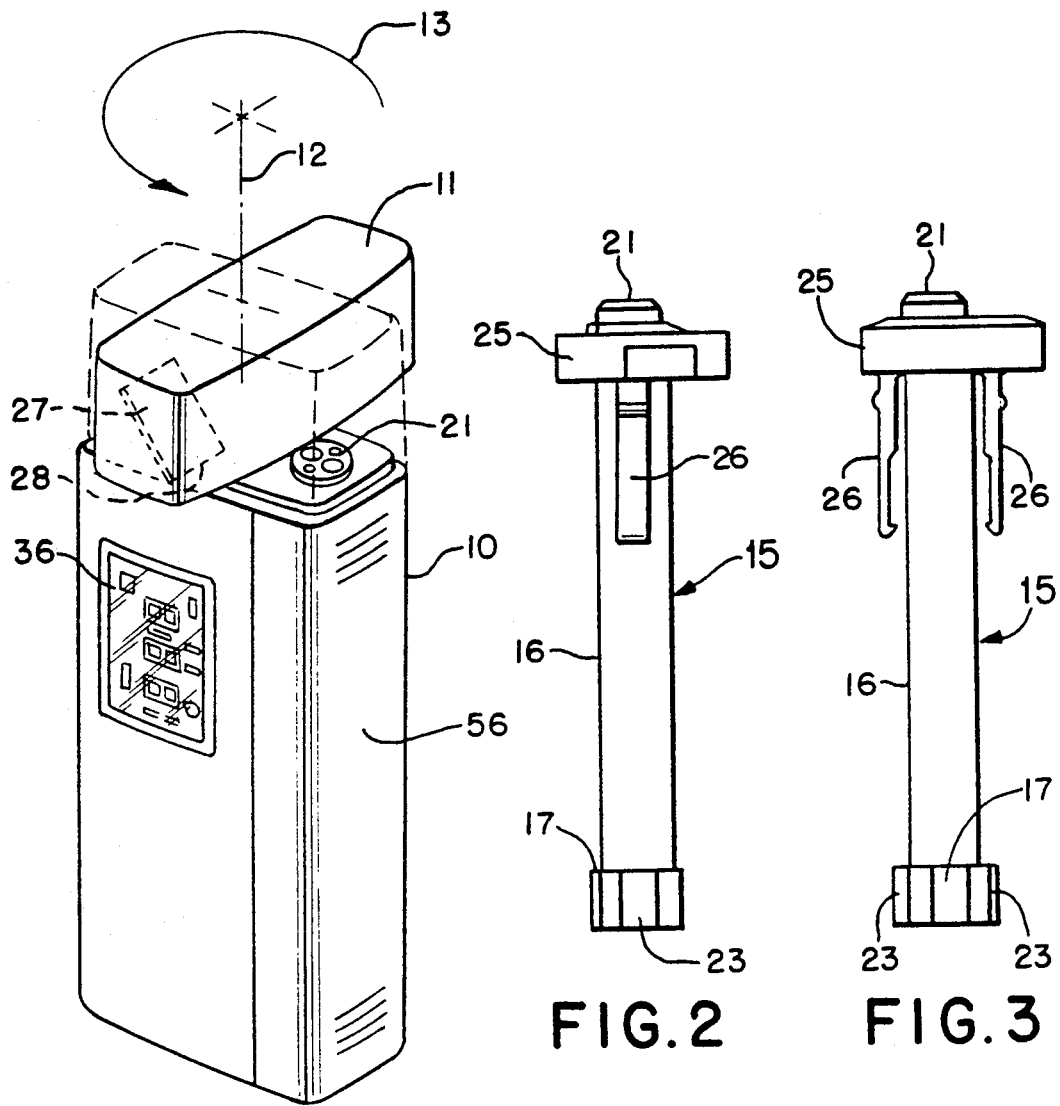
Figure 4:
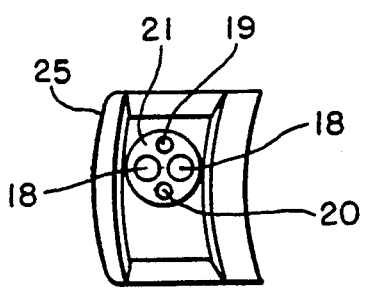
Figure 5:
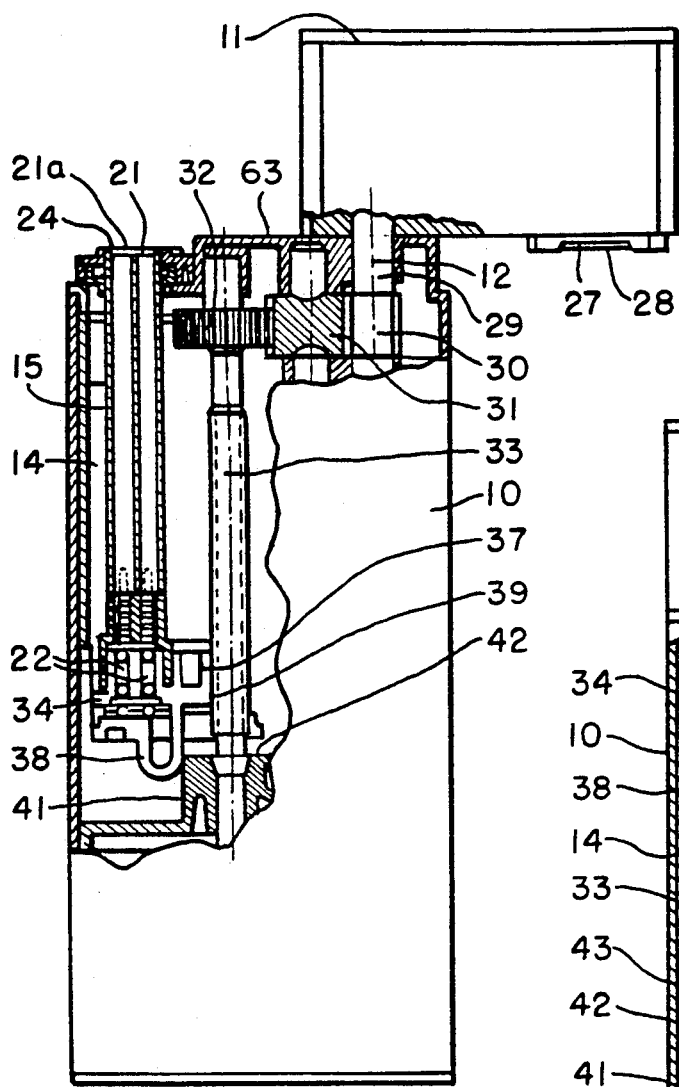
Figure 6:
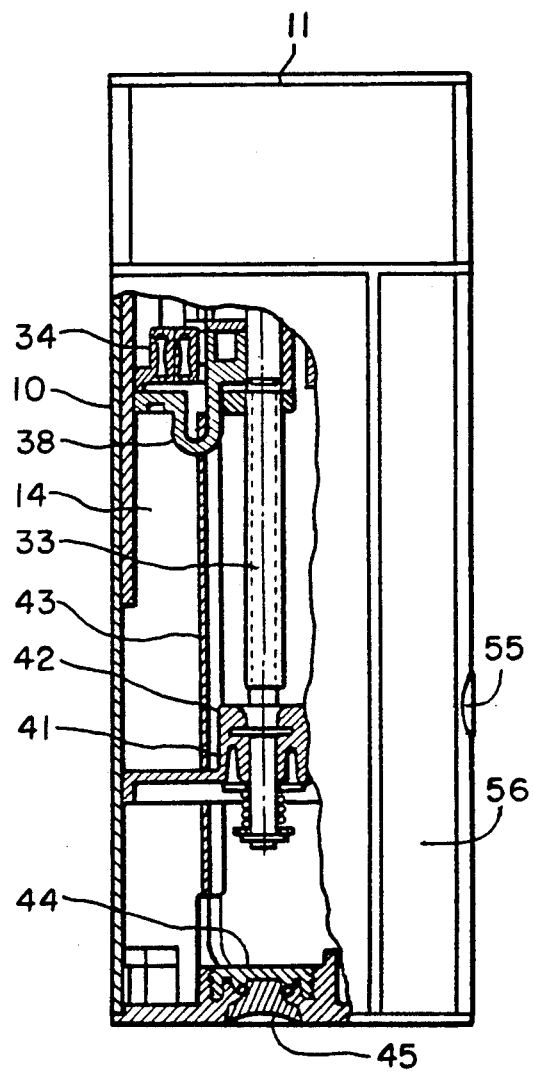
Figure 7:
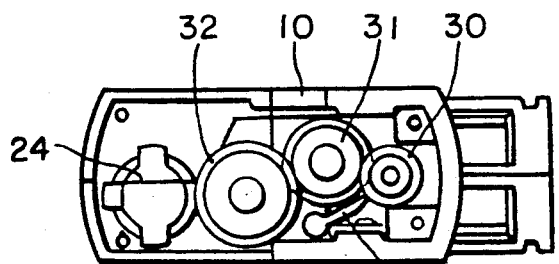
Figures 8, 9:
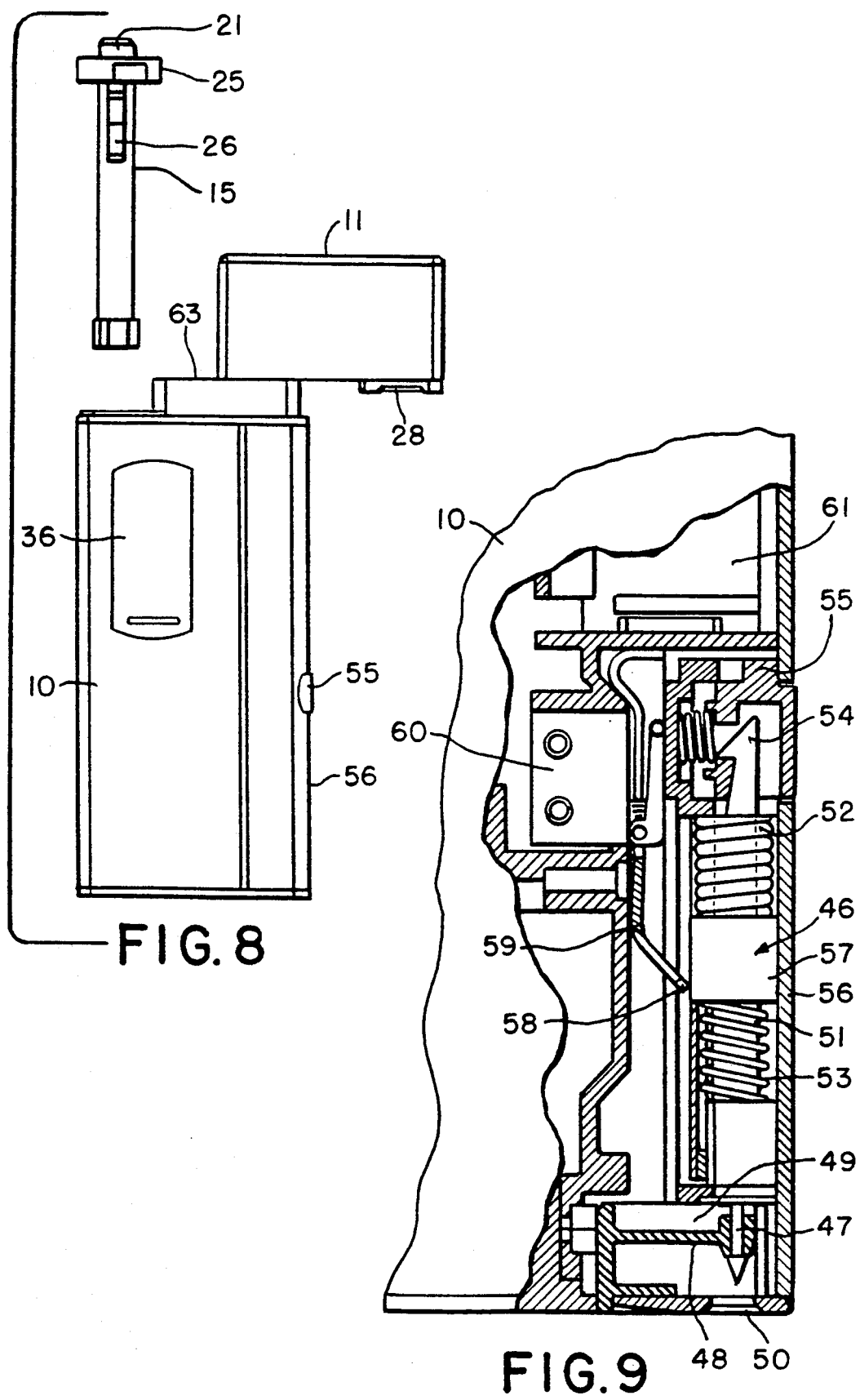
Figure 10:
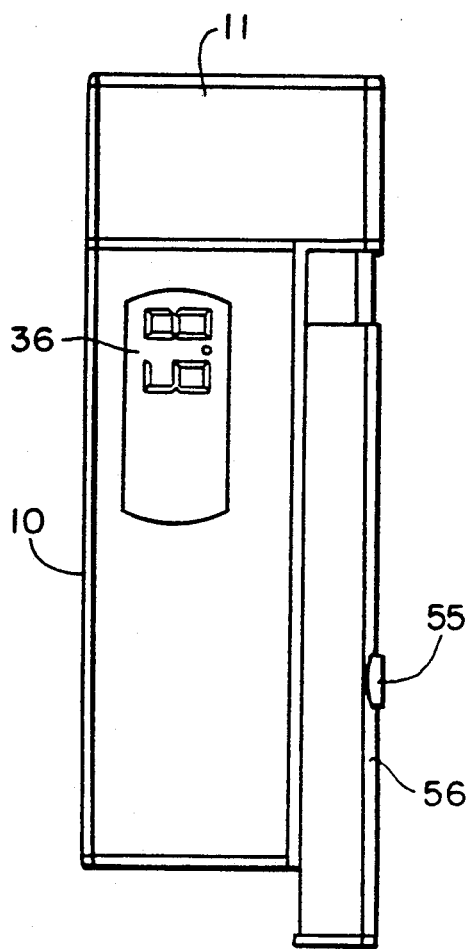
Figure 11:
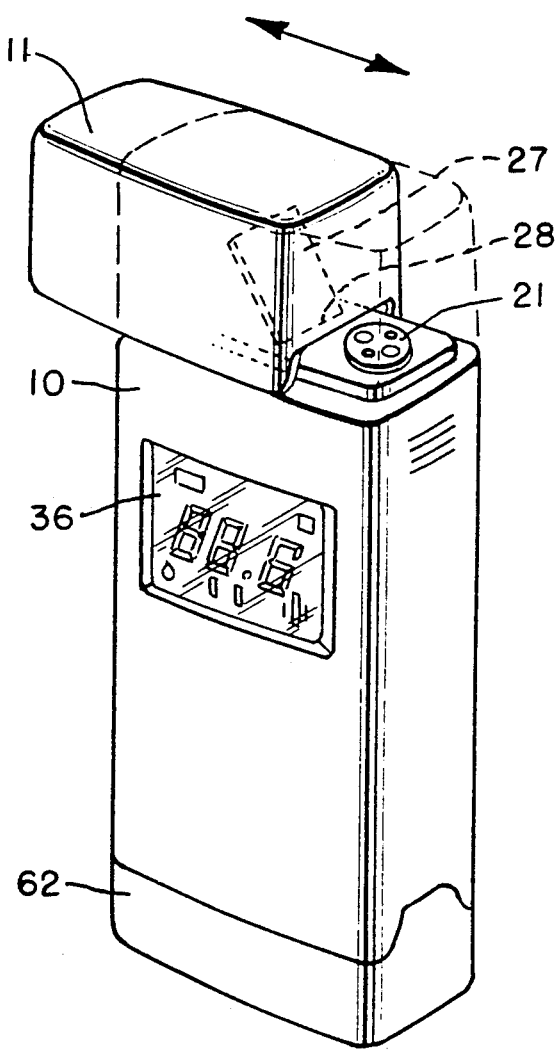
Figure 12:
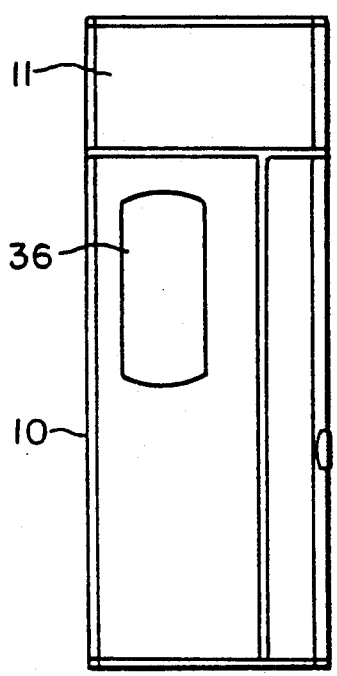
Figure 13:
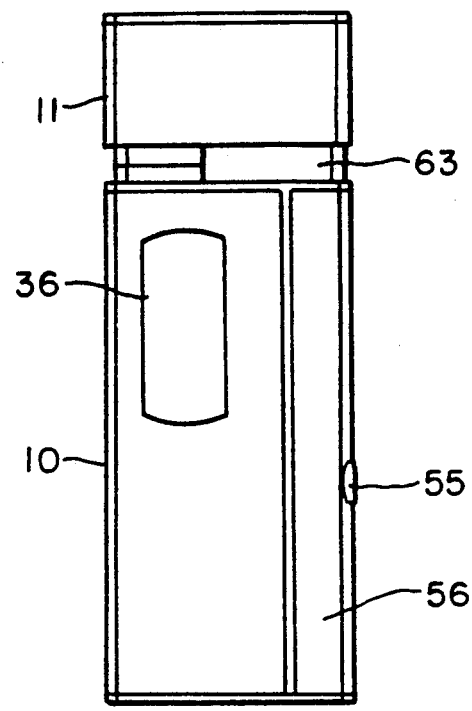
Figure 14:
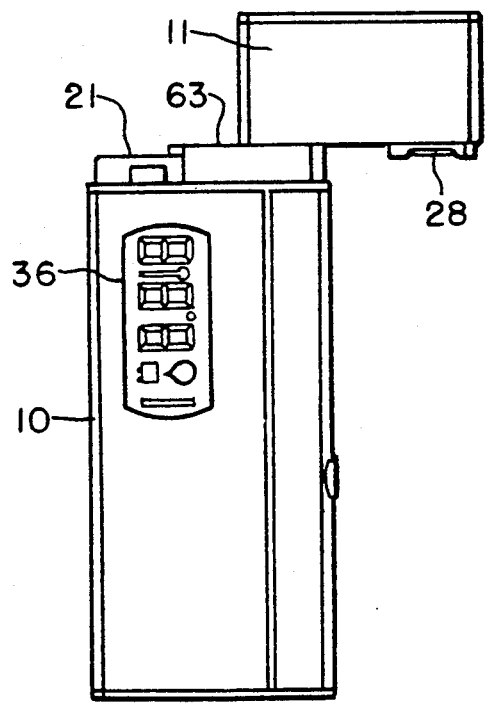
Figure 15:
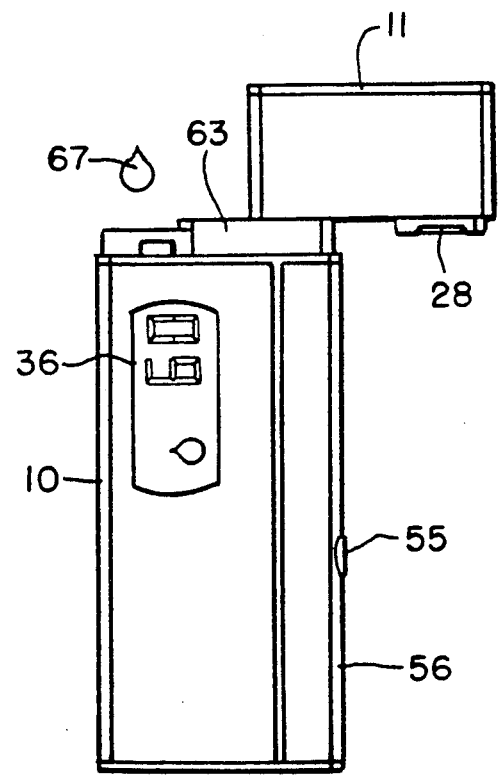
Figure 16:
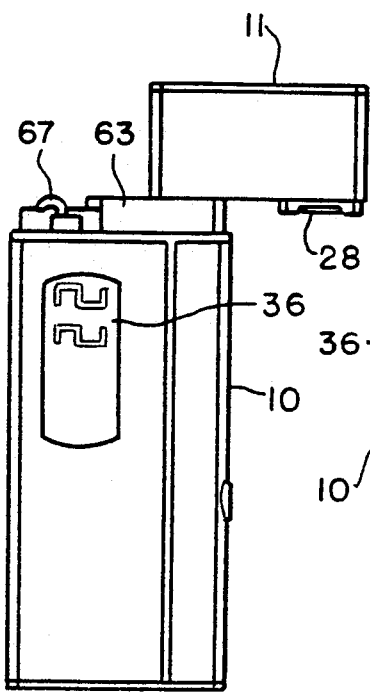
Figure 17:
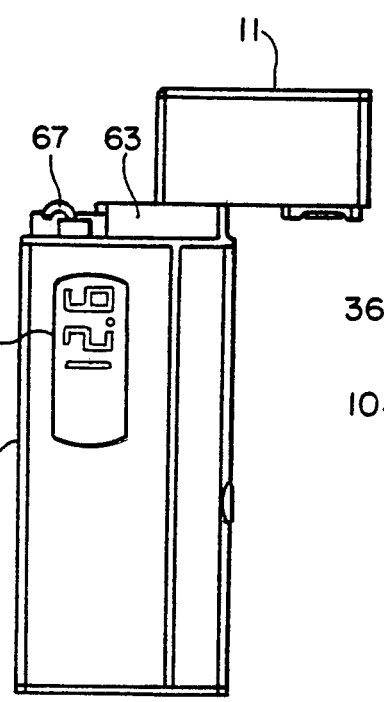
Figure 18:
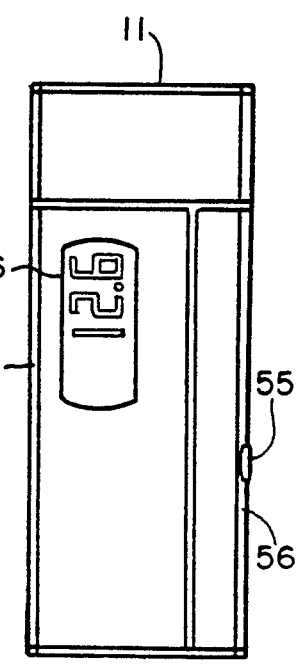
Figure 19:
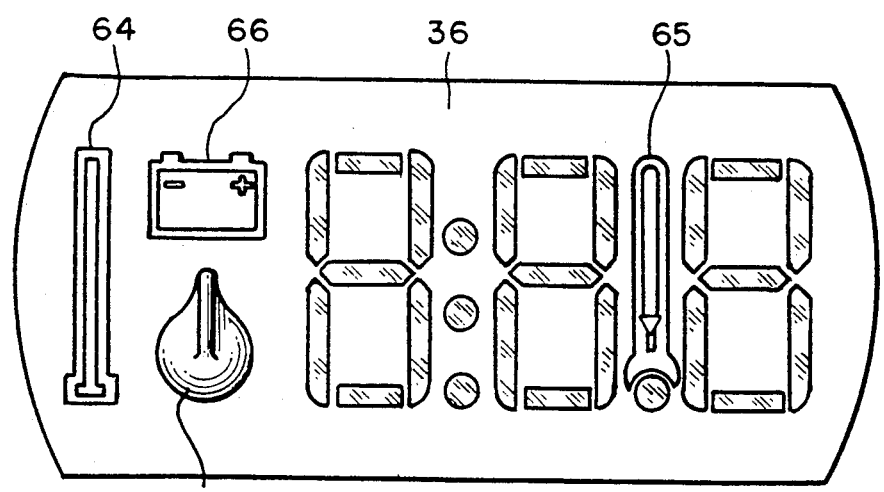
Figure 20:
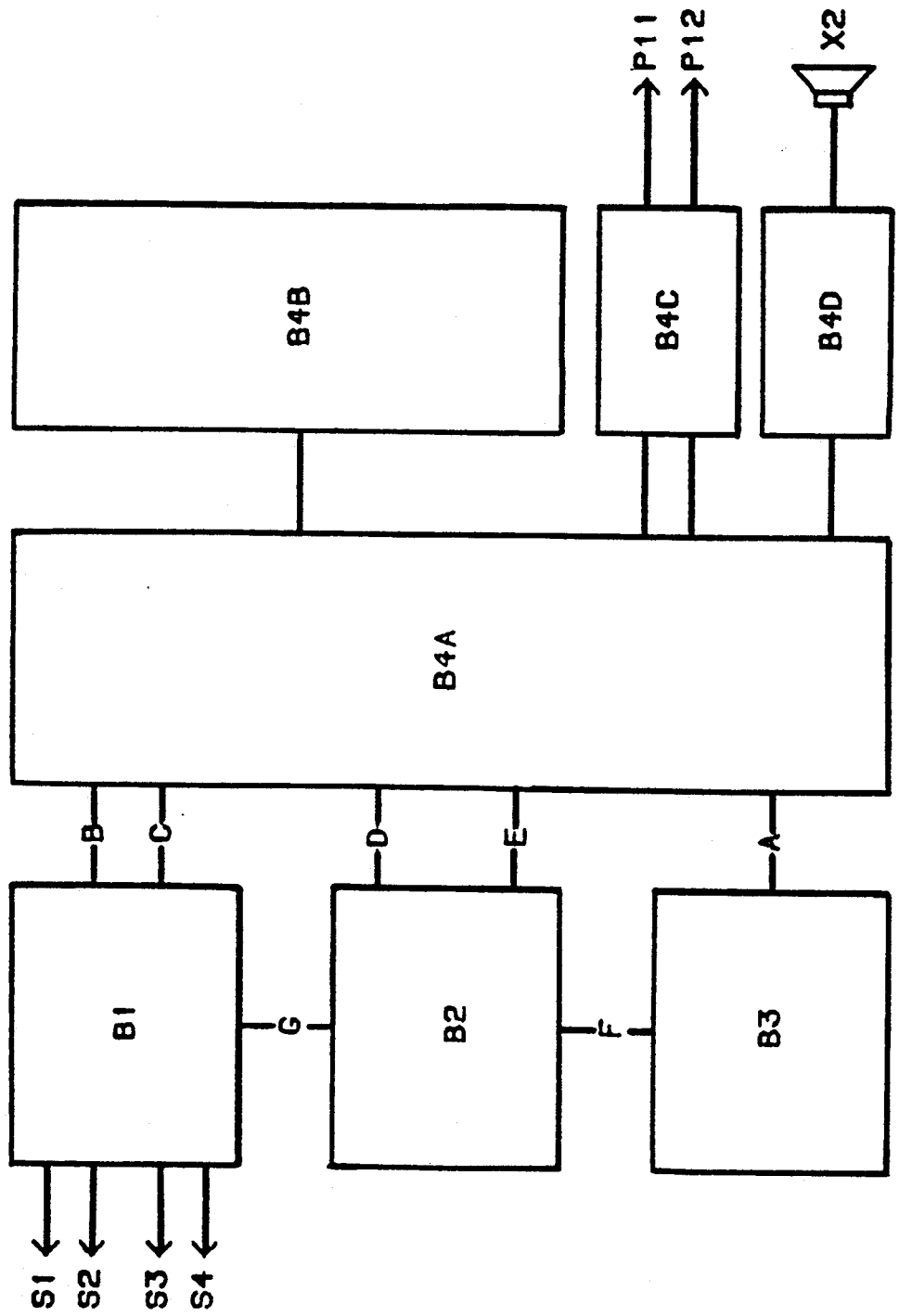
Figure 21:
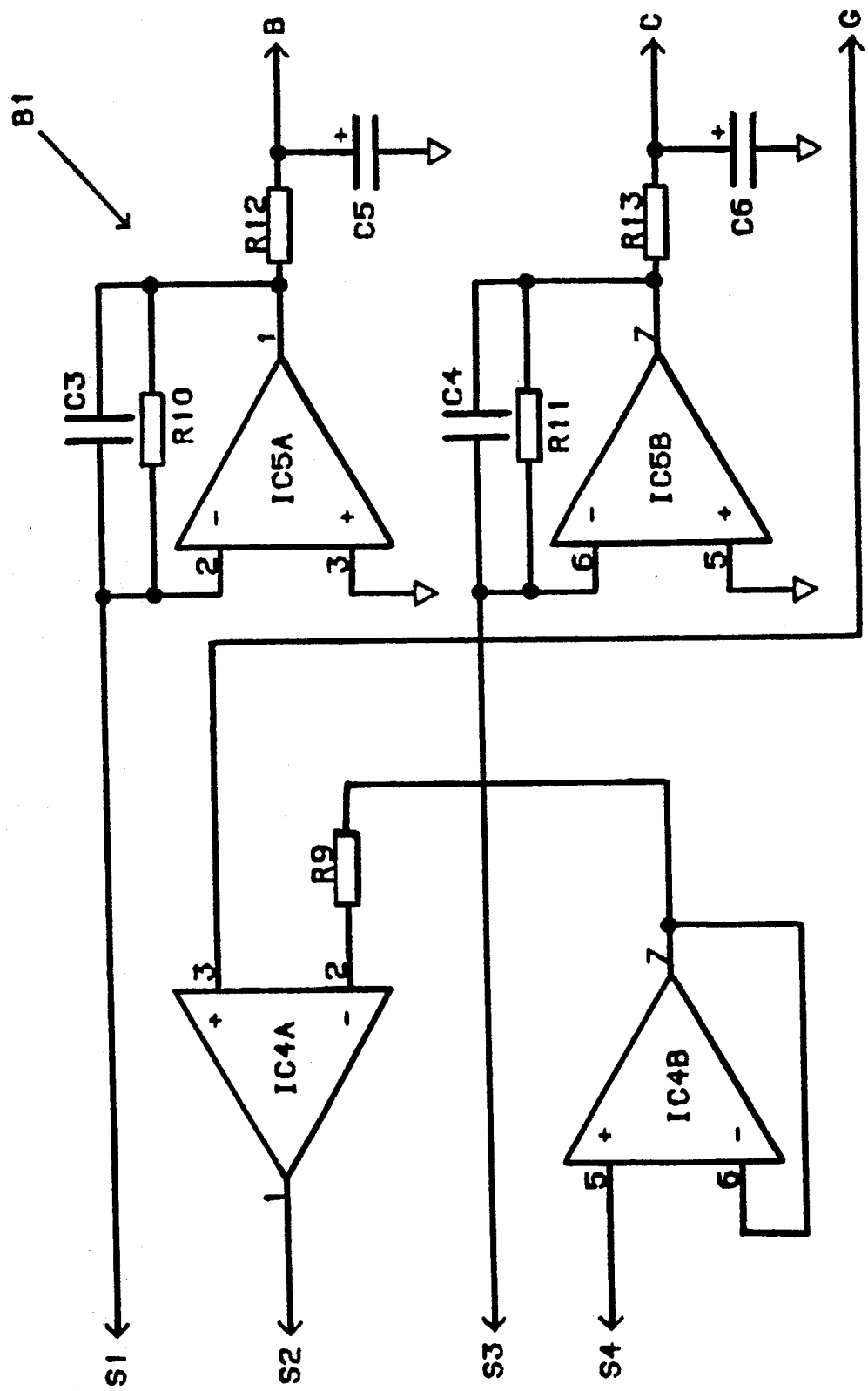
Figure 22:
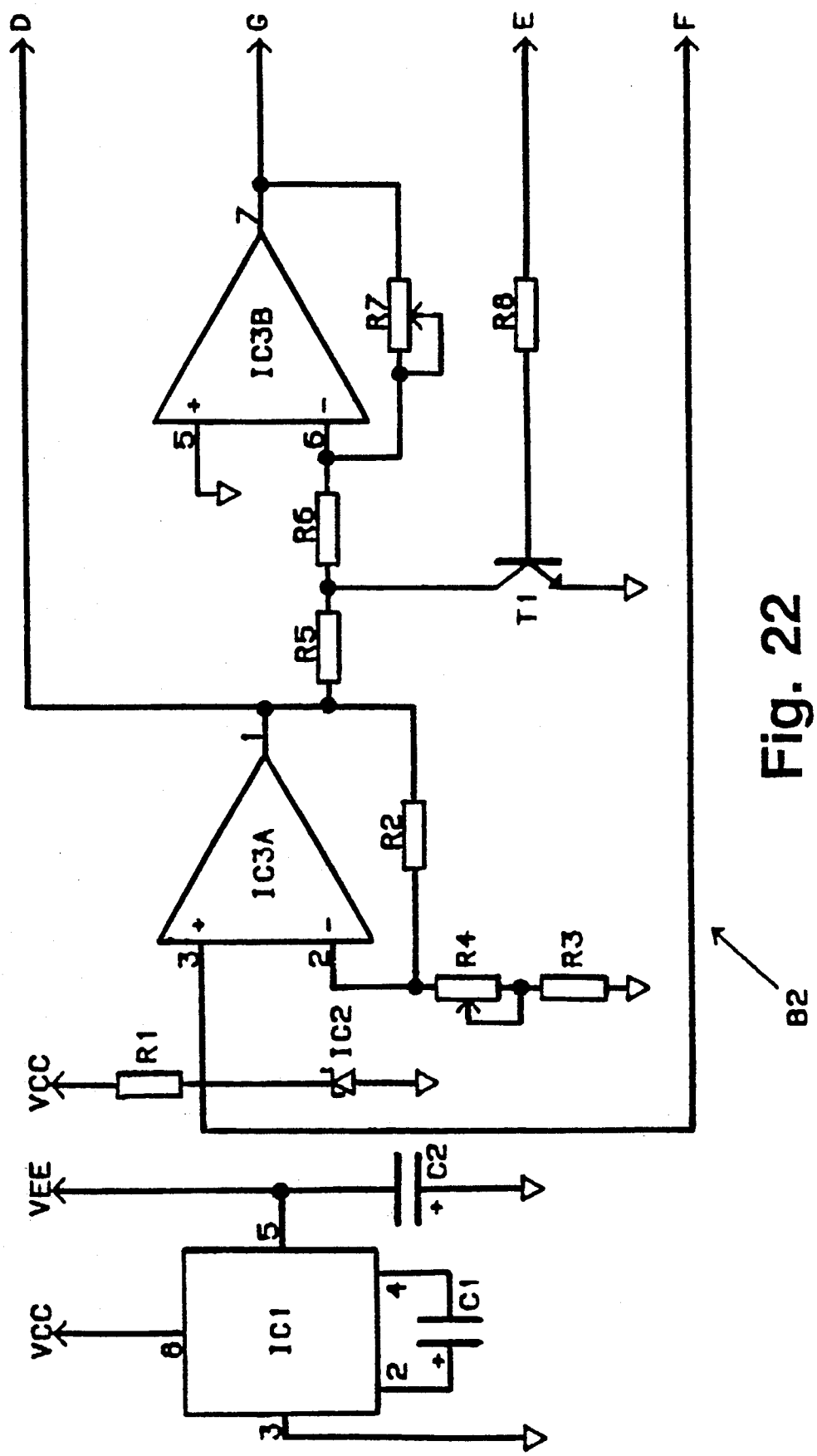
Figure 23:
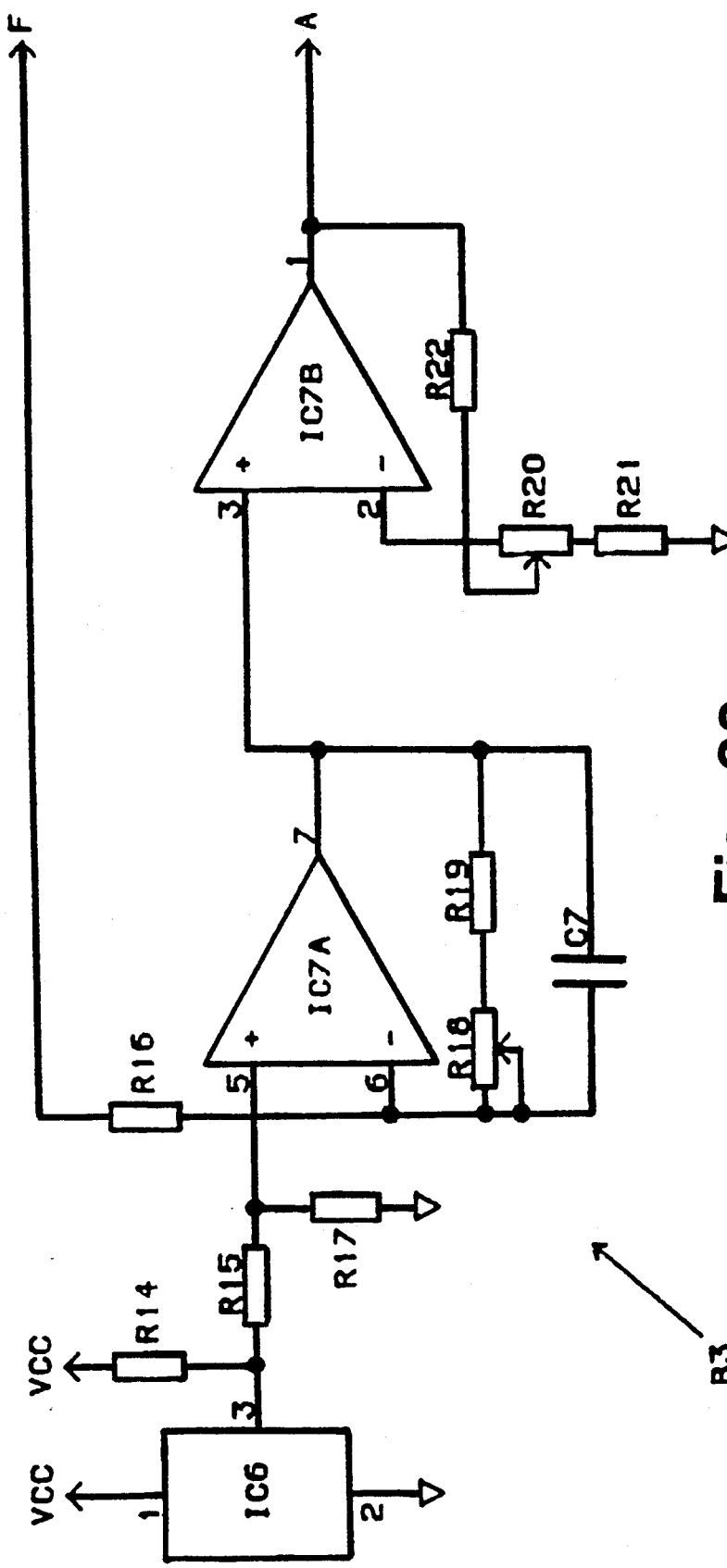
Figure 24:
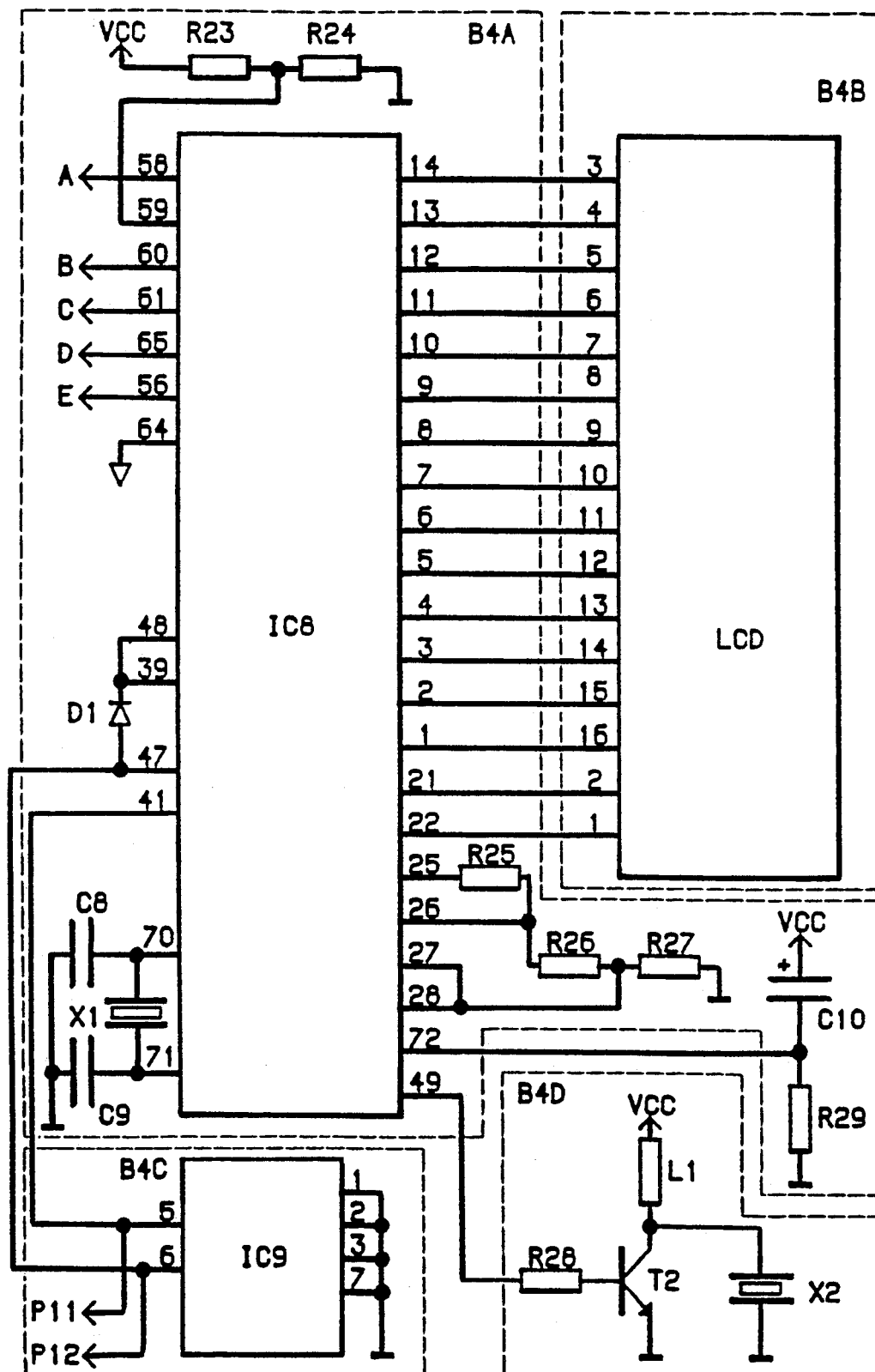
Figure 25:
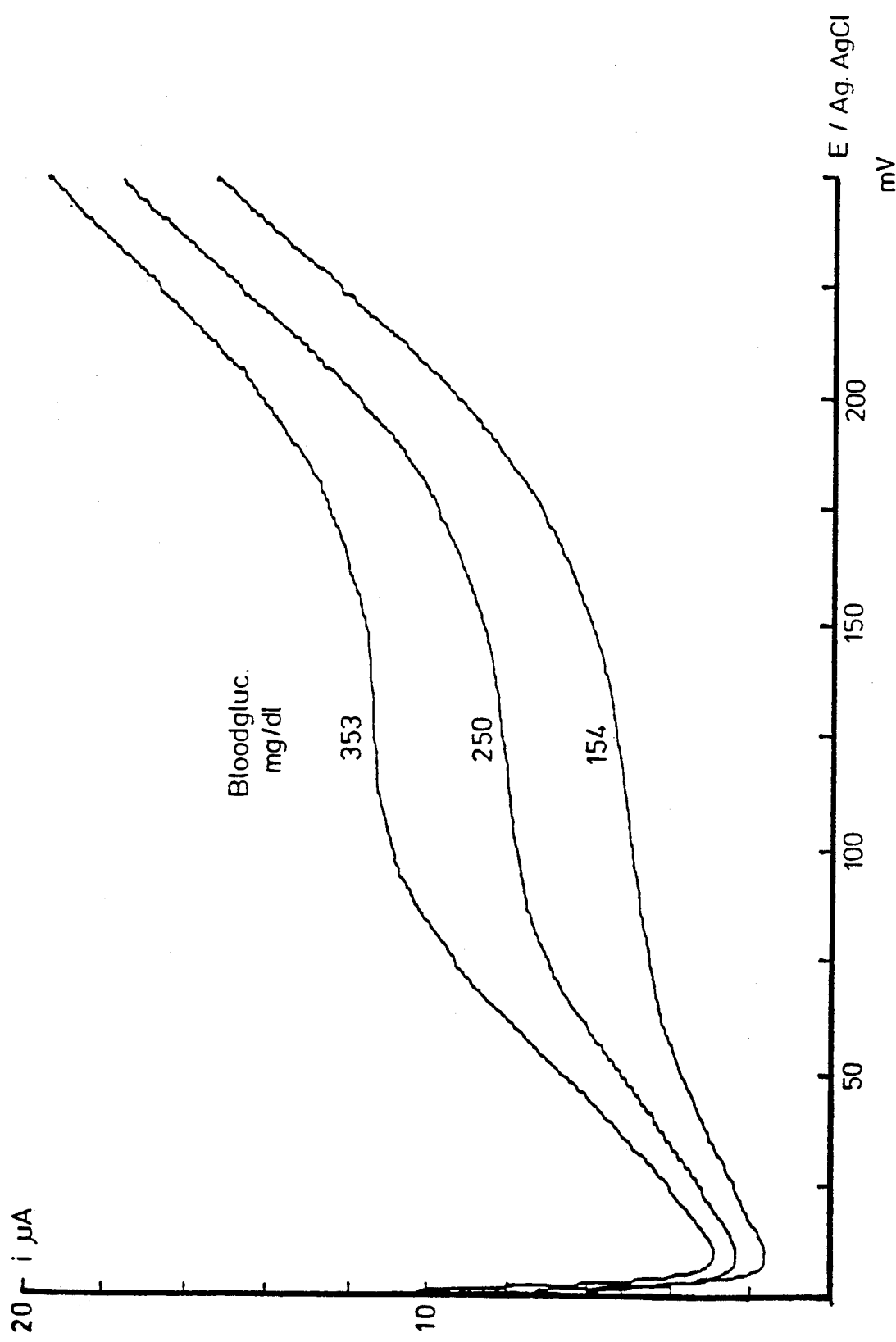
Figure 26:
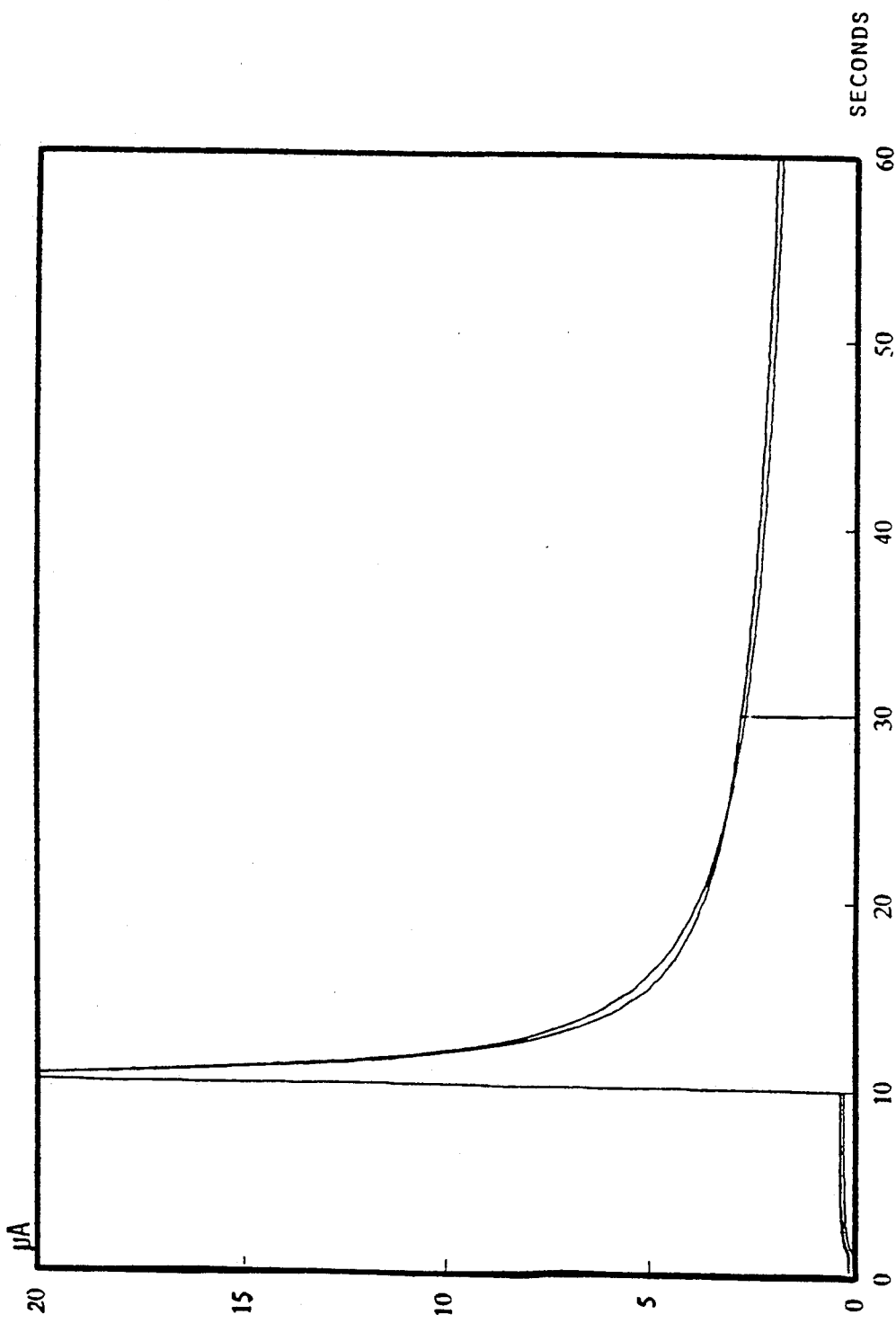
Figure 27A:
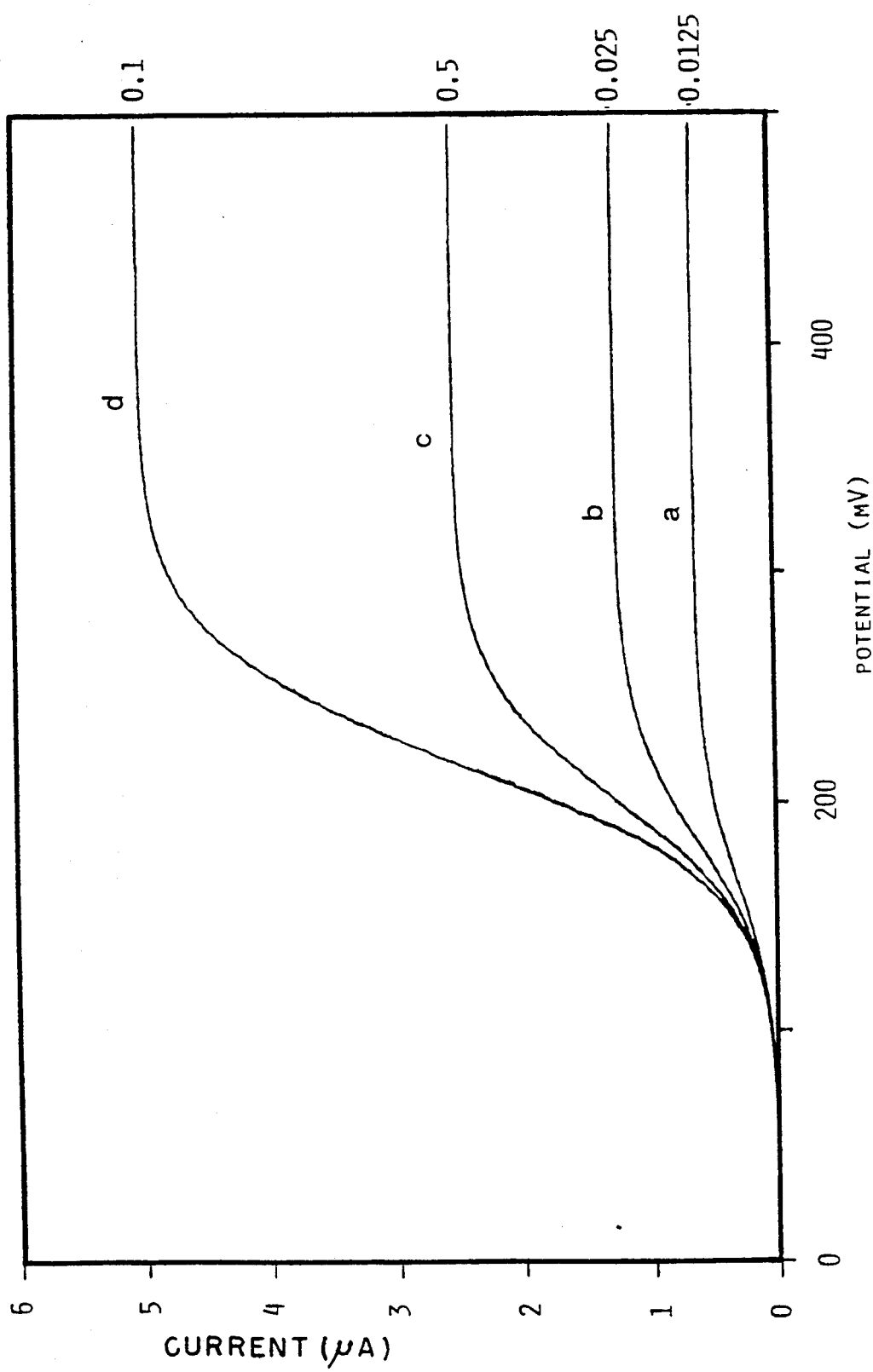
Figure 27B:
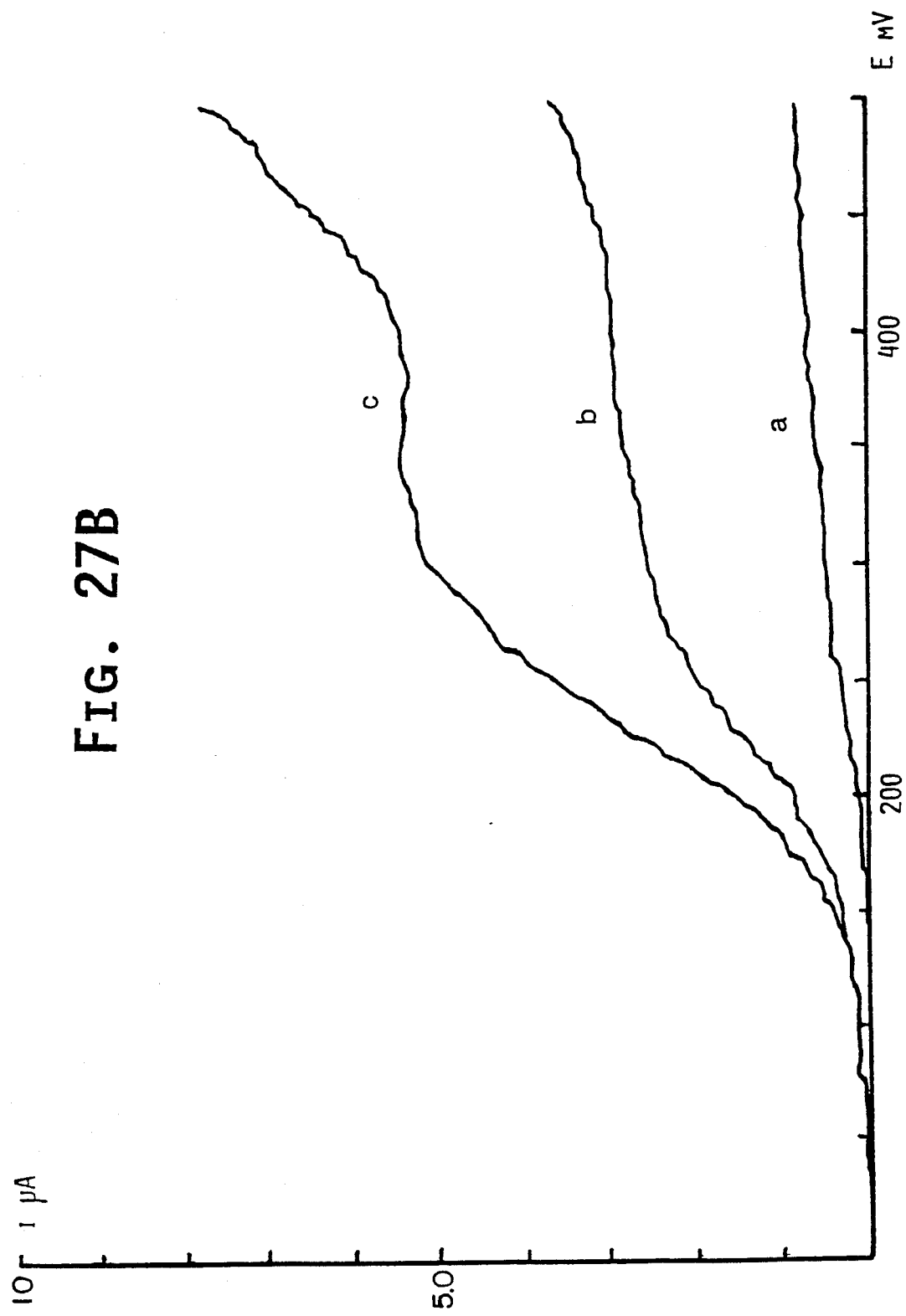
Figure 28A:
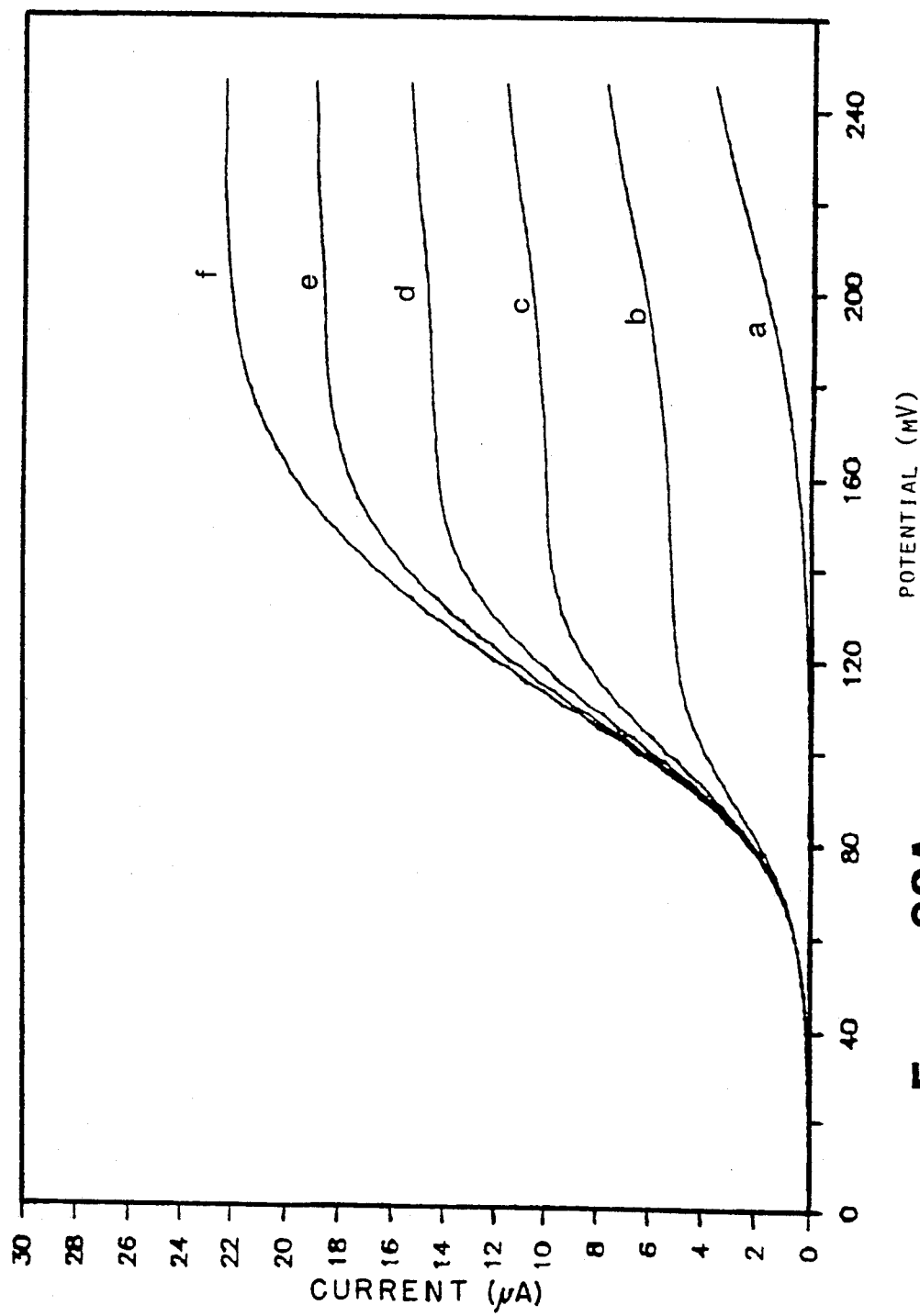
Figure 28B:
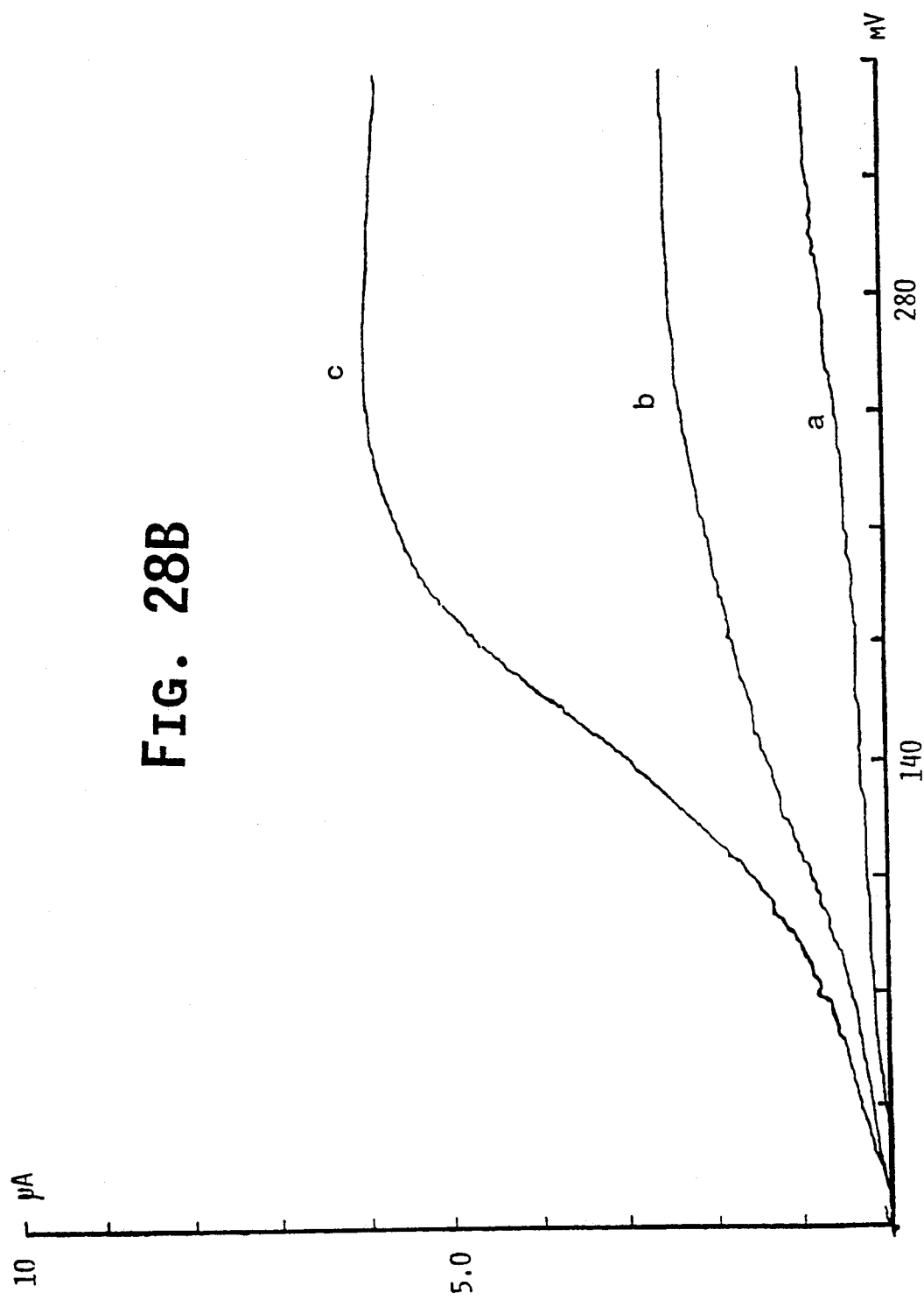
Figure 29A:
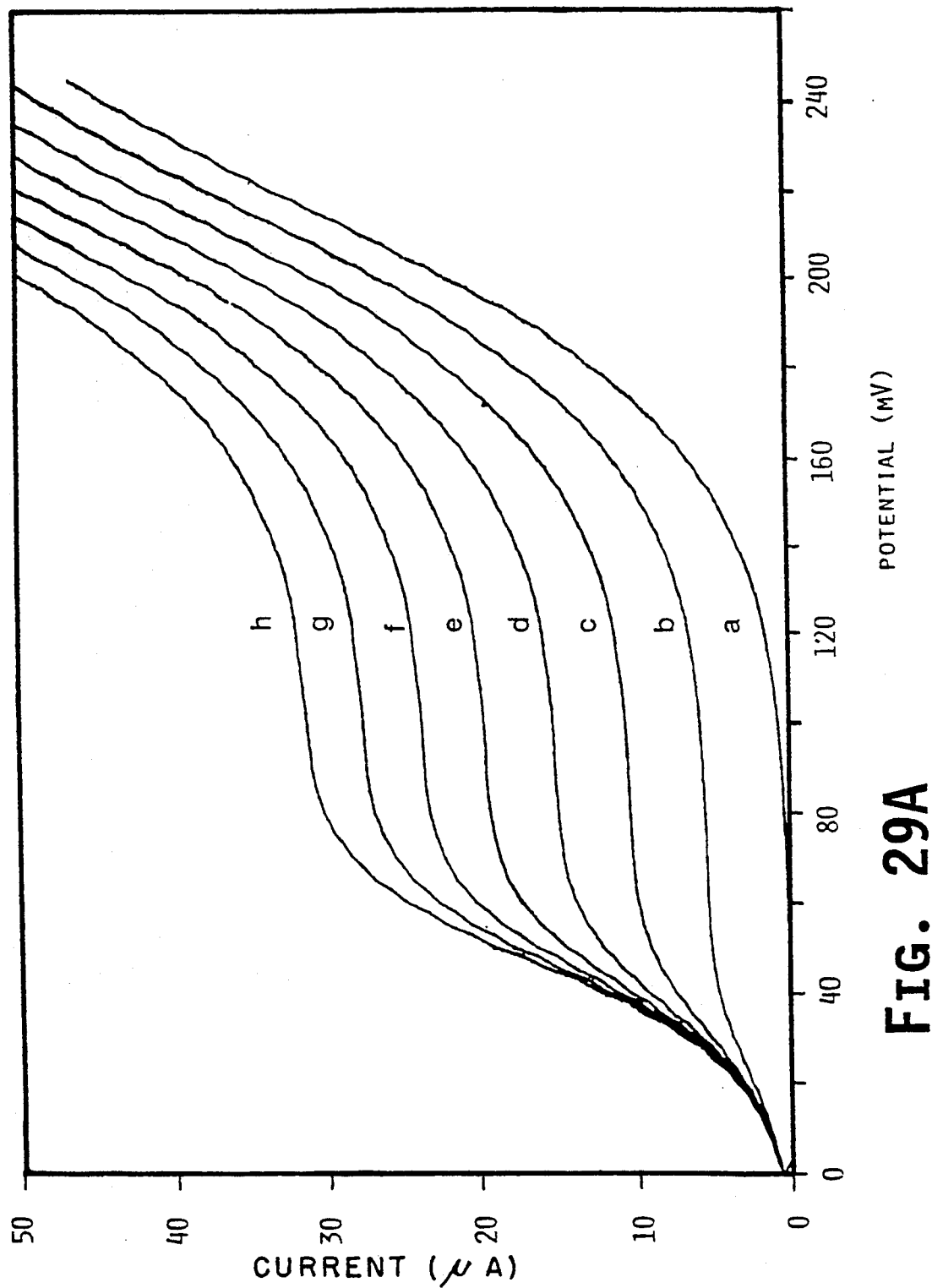
Figure 29B:
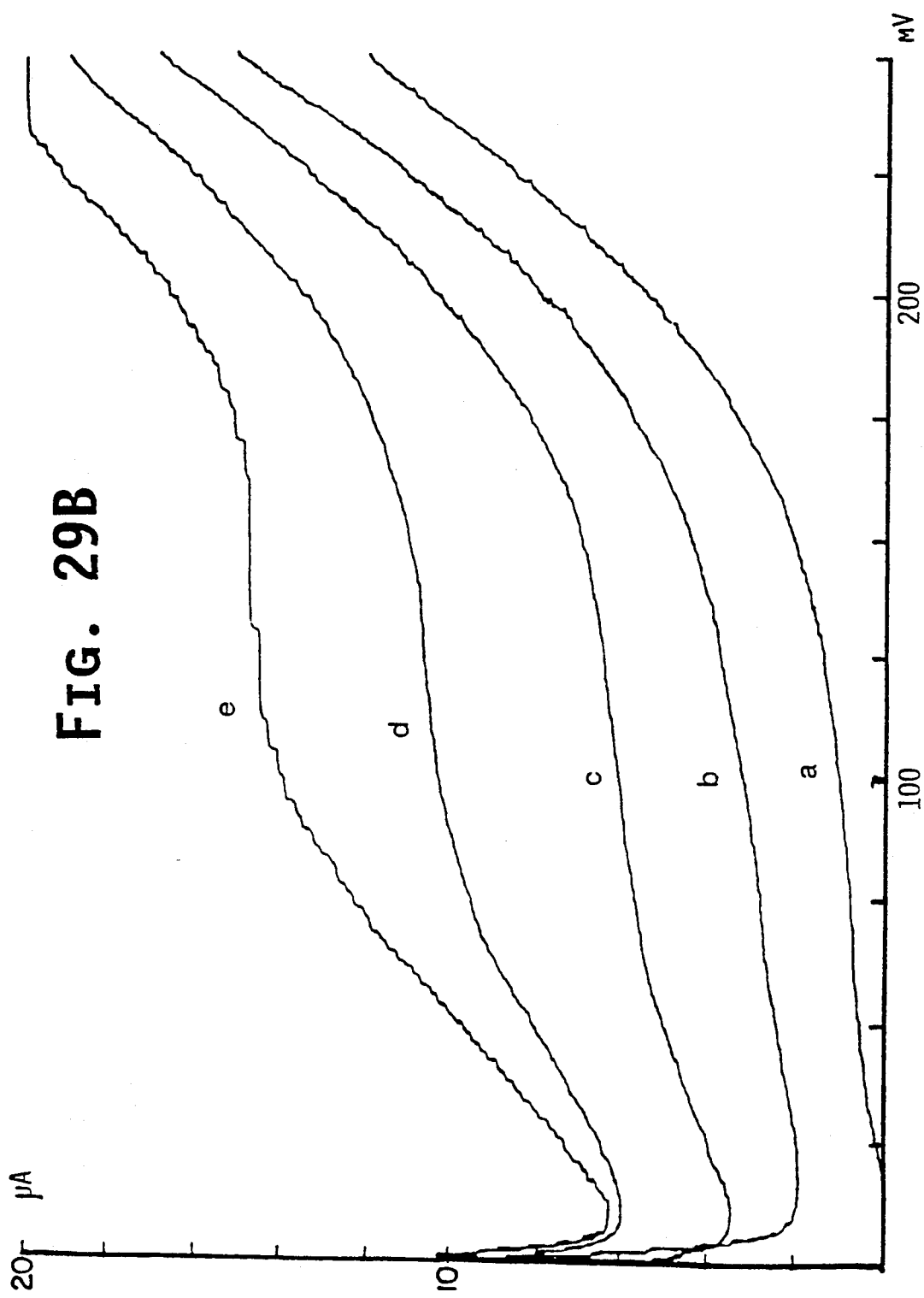
Figure 30A:
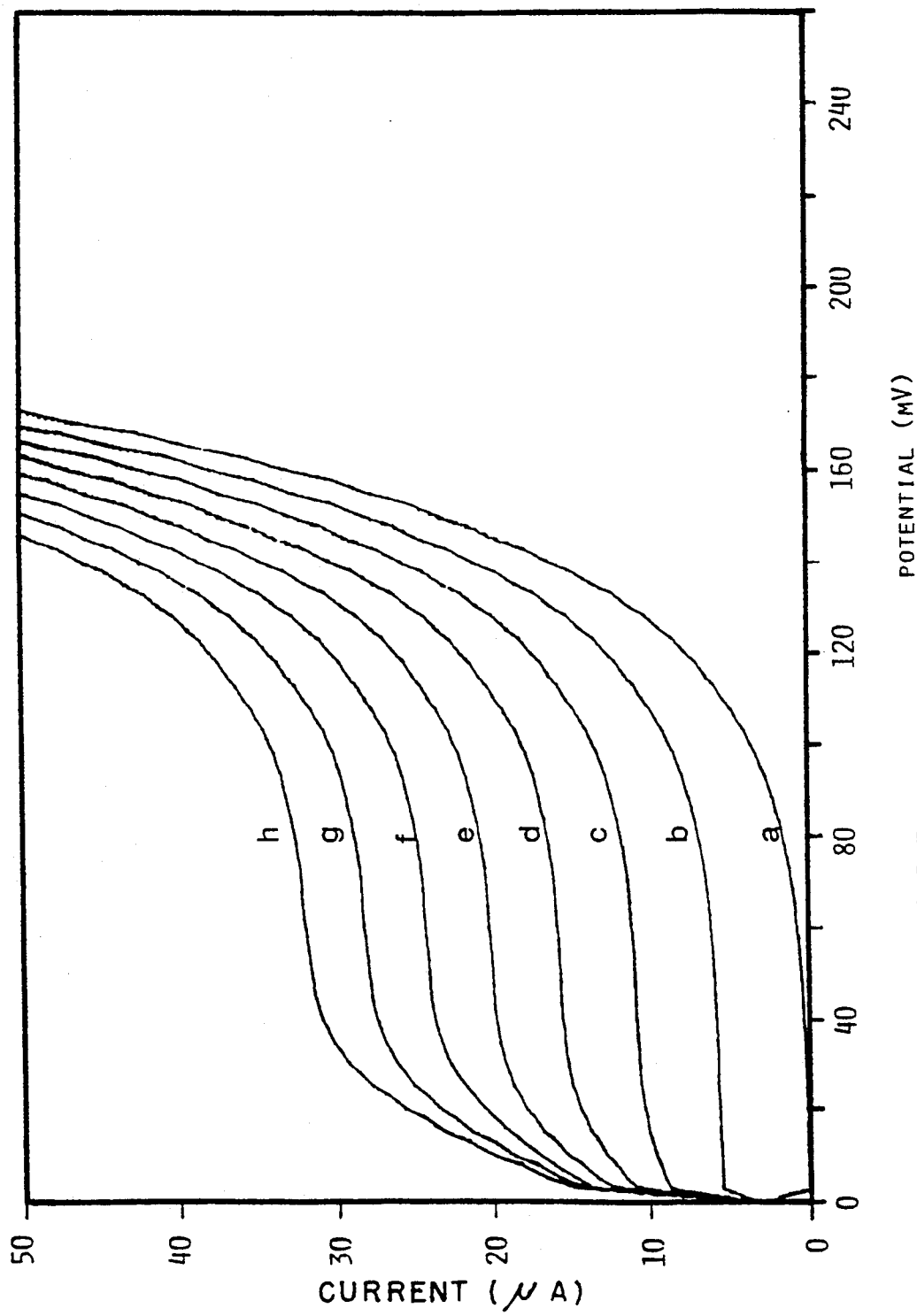
FIG. 30B shows that the operational potentials using 0.5M 1,1'-dimethylferrocene are low, being about 20-100 mV.
FIG. 30C shows that the calibration curves are linear within the range of 0-350 mg/dl glucose. The curve corresponding to an applied potential of 30 mV has an intercept equal to zero, showing that there is no appreciable interference resulting from the presence of other oxidizable substances in the blood.
Figure 30B:
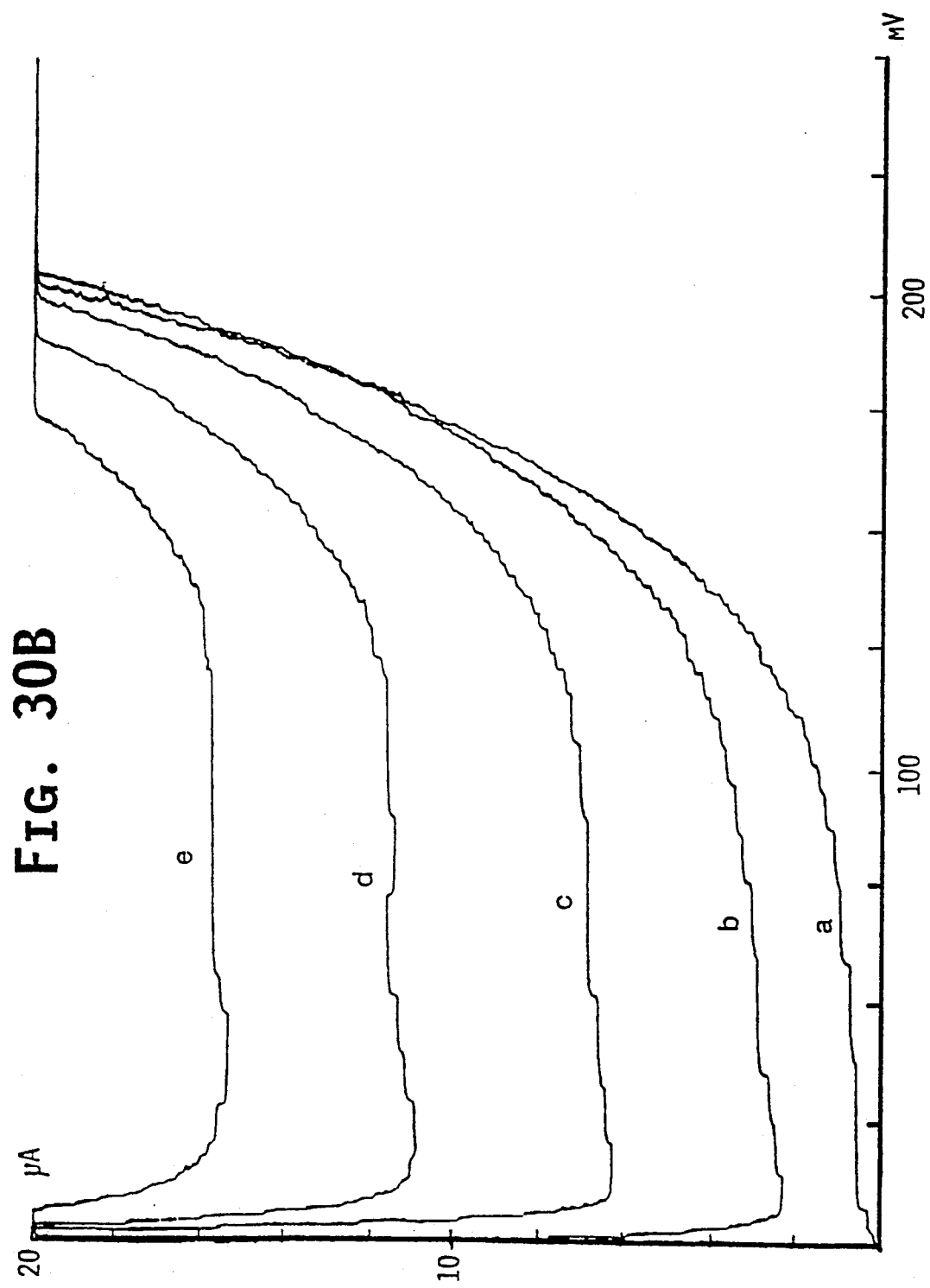
Figure 30C:
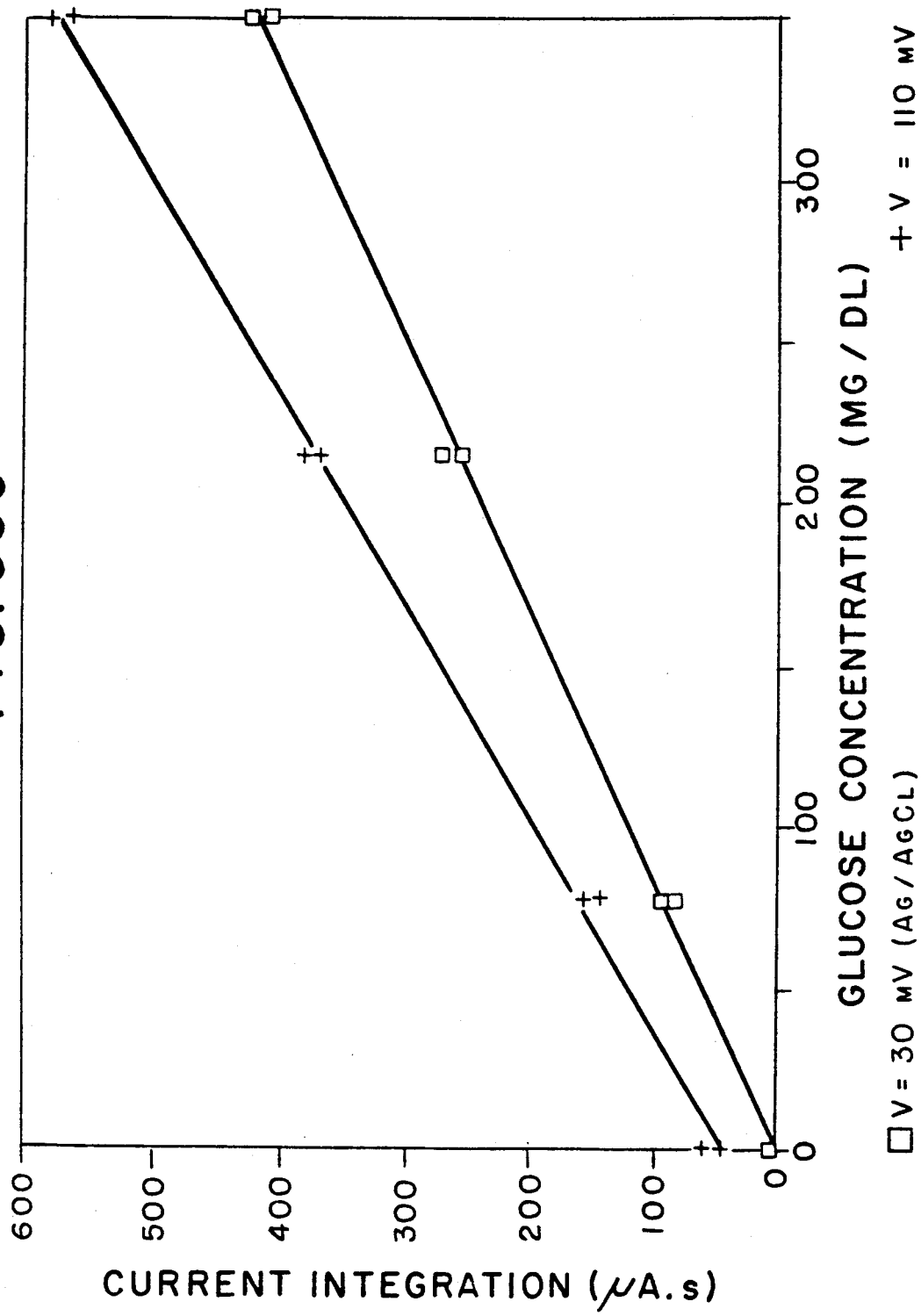

The prototype implementation of the electronic circuitry of the apparatus according to the present invention described in the legend to figures with reference to FIGS. 20-24 was implemented from the following components:

C1: Tantal capacitor SMD; 10 μF/6.3 V
C2: Tantal capacitor SMD; 10 μF/6.3 V
C3: Ceramic multilayer CAP; 33 nF
C4: Ceramic multilayer CAP; 33 nF
C5: Tantal capacitor SMD; 4.7 μF/6.3 V
C6: Tantal capacitor SMD; 4.7 μF/6.3 V
C7: Ceramic multilayer CAP; 10 nF
C8: Ceramic multilayer CAP; 22 pF
C9: Ceramic multilayer CAP; 22 pF
C10: Tantal capacitor SMD; 1 μF/10 V
D1: Shottky diode (SMD); BAT54
LCD Liquid Crystal Display; custom made
IC1: Switched capacitor voltage conv.; LTC1044
IC2: Micropower voltage reference; LT1004
IC3: Low-power bifet OP-AMP; AD648
IC4: Low-power bifet OP-AMP; AD684
IC5: Low-power bifet OP-AMP; AD648
IC6: Temperature sensor; S8100
IC7: Low-power bifet OP-AMP; AD648
IC8: Single chip microcomputer 4-bit; μPD75328
IC9: E$^2$PROM; X24LC16
T1: Transistor; BC849
T2: Transistor; BC849
L1: Booster coil
R1: 100 kΩ
R2: 100 kΩ/1%
R3: 90.1 kΩ/1%
R4: 10 kΩ/TRIM
R5: 47 kΩ/1%
R6: 47 kΩ/1%
R7: 10 kΩ/TRIM
R8: 100 kΩ/1%
R9: 47 kΩ/1%
R10: 240 kΩ/1%
R11: 240 kΩ/1%
R12: 47 kΩ/1%
R13: 47 kΩ/1%
R14: 1MΩ/1%
R15: 1MΩ/1%
R16: 1MΩ/1%
R17: 1MΩ/1%
R18: 200 kΩ/TRIM
R19: 1.2MΩ/1%
R20: 10 kΩ/TRIM
R21: 39 kΩ/1%
R22: 200 kΩ/1%
R23: 100 kΩ/1%
R24: 100 kΩ/1%
R25: 120 kΩ/1%
R26: 100 kΩ/1%
R27: 100 kΩ/1%
R28: 47 kΩ/1%
R29: 1MΩ/1%
$X_1$: Resonator Crystal 4.1943 MHz
$X_2$: Piezo buzzer The above described prototype implementation of the electronic circuitry of the apparatus according to the present invention is to be converted into a custom designed large-scale integrated circuit, in which components and functions identical to or similar to those of the prototype implementation are incorporated. The following features are to be underlined.

The electronic circuit is adapted to carry out the calculation of a measuring result on the basis of the analog measuring signals from a routine in which firstly the temperature detected by the temperature sensor and secondly the specific characteristics of the measuring assembly presently mounted in the apparatus are taken into consideration, which characteristics are input to the microprocessor from the E$^2$PROM IC9 of the block B4C. By the adaptation of the calculation routine to the characteristics of the present electrode device, the electrode device may be manufactured at less critical tolerance ranges, which are compensated for in the specific measuring set-up by the modification of the calculation routine by the characteristics or parameters of the present electrode device and in particular in the present material composition etc. of the measuring electrode material. The electronic circuit is further adapted to continuously measure the temperature in order to determine whether the electrode device is at any time exposed to excessively low or high temperatures beyond a temperature range within the electrode device is to be permanently maintained in order to ensure that the material of the measuring and sensor electrodes is not damaged due to exposure to low or high temperatures. To this end, the entire electronic circuitry is permanently turned on, however, at a low power consumption mode, in which the temperature sensor and the electronic circuitry connected thereto are permanently supplied with power, while the microprocessor periodically shifts from a low power consumption mode to a normal operational mode, in which the microprocessor checks whether the temperature sensor has generated a signal representing an excessively low or high temperature. In case the temperature sensor and consequently the electrode device have been exposed too low or too high temperatures, the microprocessor IC8 outputs an alarm to the display block B4B and is turned in a blocking mode in which the microprocessor refuses to carry out a calculation of a measuring result in case the operator attempts to use the apparatus for determining the glucose content of a blood sample.

The microprocessor IC8 automatically registers when the sample is applied to the sensor electrode, by detecting the presence of the short-circuiting condition between the electrodes of the electrode device, thereby avoiding any problems associated with a need to follow a specified timing sequence.

In the large-scale custom designed integrated implementation of the electronic circuitry, the microprocessor is further connected to an internal storage, such as an additional $E^2PROM$, in which data representing calibration parameters of the individual operation amplifiers, voltage references, temperature sensor, etc. are stored, as well as measurement results.

It has further been realised that a highly accurate temperature sensor may be provided from a crystal oscillator, as the crystal oscillator is a temperature dependent device, which generates a clock frequency dependent on the temperature to which the crystal is exposed. Experiments have confirmed that a highly accurate temperature sensor may be provided from a crystal oscillator, the output signal of which is representative of the temperature to which the crystal is exposed. The above-mentioned additional $E^2PROM$ may further include data representing calibration parameters of the temperature sensitive crystal oscillator.

EXAMPLE 2

Preparation of the graphite paste of the sensor electrode 1. step: surface oxidation of the graphite powder:

The carbon particles are heated at 100° C. for 40 hours in a continuously rotated flask which is well ventilated by clean, dry atmospheric air, 2. step carbon activation:

42.3 mg of 1-cyclohexyl-3-(2-morpholinoethyl)carbodiimidemetho-p-toluenesulfonate (N-cyclohexyl-N'-β[N-methylmorpholino)ethyl]carboddimide p-toluenesulfonate salt) is dissolved in 3 ml of acetic acid/acetate buffer of pH 4.76. The solution is mixed with 1 gram of oxidized graphite particles from step 1. The mixture is continuously stirred at room temperature for 2 hours. Then the mixture is washed 7 times with distilled water and dried by evaporation of the solvent at room temperature or by lyophilization.

3. step enzyme immobilization:

8000 IU glucose oxidase per gram activated graphite is dissolved in 2 ml phosphate buffer pH 7.3 per gram carbodiimide-activated graphite. The mixture is continuously stirred at 4° C. for 16 hours. Then the mixture is dried by evaporation of the solvent at room temperature or by lyophilization. The dry powder is sieved through a 48 mesh nylon sieve.

4. step 0.6 ml of paraffin oil is mixed with 4-5 ml of petroleum ether or n-pentane per gram activated graphite. 12.8 mg 1,1'-dimethylferrocene is dissolved in this mixture.

5. step

The activated graphite particles comprising the immobilized enzyme from step 3 is mixed with the mixture from step 4 followed by evaporation at room temperature of the petroleum ether or the n-pentane.

6. step filling of the channels in the electrode body;

The mixture from step 5 is filled into the channel(s) of the sensor electrode in vacuo.

EXAMPLE 3

Preparation of the sensor electrode, the reference electrode and the counter electrode and the filling of the electrodes into the electrode device body In the following is described the preparation of the electrodes of an electrode device comprising four electrodes, each filled into a channel of the electrode device body. The electrodes are two sensor electrodes, a reference electrode and a counter electrode.

Counter electrode and reference electrode

The counter electrode and the reference electrode channels are filled with 0.2 mm of silver wire and 0.2 mm of silver wire coated with a layer of silver chloride, respectively. The coating of the silver wire with silver chloride to obtain the reference electrode is done by placing the silver wire in a 1% w/w solution of ferric chloride (Merck art. 3943) in a 1M solution of hydrogen chloride (Merck art. 317) for about 30 min. Then the silver wire coated with silver chloride (reference electrode) and the silver wire (counter electrode) are fixed in a plug of brass in the bottom of the reference electrode channel and the counter electrode channel, respectively, in the electrode device body and the fixation in the channels is done by application of a two-component epoxy adhesive. The application is done using a 5 ml syringe and a 18G needle and precautions are made to remove any gas present in the channel. The two-component epoxy adhesive is prepared substantially immediately before use by mixing 4 parts of glue with 1 part of hardener.

After one day, the two-component epoxy adhesive has stiffened and the electrode device body comprising the counter electrode and the reference electrode can be filled with the sensor electrode material.

Graphite-containing paste

Oxidation of the graphite particles

A suitable amount of graphite particles (Fluka art. 50870) are weighed and charged into a flask which is placed in a Rotavapor. The graphite particles are oxidized by means of dry atmospheric air for at least 48 hours, the air being substituted with 99.9% pure atmospheric air under pressure. The oxidation takes place at 100° C. by means of a termostated bath of silicone oil. In order to ensure an optimal movement in the graphite particles, a few small bullets of teflon is added to the flask containing the graphite particles.

Carbodiimide activation

The carbodiimide (1-cyclohexyl-3-(2-morpholinoethyl)carbodiimidemetho-p-toluenesulfonate) (Sigma art. C-1011) is used in an amount corresponding to 0.1 mol per gram surface oxidized graphite particles, the amount being equivalent to 42.36 mg carbodiimide per gram surface oxidized graphite particles.

The appropriate amount is dissolved in 2-3 ml of 0.05M acetate buffer per gram oxidized graphite.

The acetate buffer is prepared from 2.05 g sodium acetate (Merck art. 6268) and 1.50 g = 1.43 ml glacial acetic acid (Merck art. 63) per liter buffer. pH is adjusted to 4.76 by addition of sodium hydroxide or acetic acid.

The volume to dissolve the carbodiimide is not critical, but the pH has to be about 4.76 in order to achieve a correct coupling of the carbodiimide to the graphite particles.

The dissolved carbodiimide is added to the oxidized graphite particles and the mixture is continuously rotated on Rotavapor for about 2 hours at room temperature. Then the excess of carbodiimide is removed by centrifugation of the mixture for 5 min at 1500 rpm and subsequently the supernatant is discarded. The residue is washed with distilled water and the mixture is re-centrifuged. The latter step is repeated until pH in the washings has increased from 4.76 to 5-6.

The oxidized and carbodiimide-activated graphite particles prepared in the above-mentioned way, is air dried by means of a ventilator and when the powder is dry, the graphite particles can be loaded with the enzyme. An appropriate drying of the particles is controlled by two subsequent weighings with an interval of 10 min. Substantially equal results indicate that the particles are dry.

The carbodiimide-activated graphite particles can not be stored but must be used shortly after the preparation.

Immobilization of enzyme on the graphite particles

In the following all reagents, solutions and utensils should have a temperature of 4° C. to avoid any denaturation of the enzyme or loss of activity during the preparation.

Glucose oxidase (type IV, Sigma art. G-2133) is used in an amount corresponding to 8000 IU/g carbodiimide-activated graphite particles. The appropriate amount is dissolved in 1 ml of 0.05M phosphate buffer solution and 0.1 ml 4% w/w aqueous solution of glutaraldehyde is added per gram carbodiimide-activated graphite particles.

The phosphate buffer is made of 4.45 g $Na_2HPO_4$ (Merck art. 6580) and 3.45 g $NaH_2PO_4$ (Merck art. 6346) per liter buffer solution. pH is adjusted to 7.30.

The 4% w/w solution of glutaraldehyde is made by diluting a 25% w/w solution (Serva art. 23114) with distilled water.

The dried carbodiimide-activated graphite particles are weighed and charged into a flask and then the solution containing the enzyme is added. After mixing at 4° C. for at least 16 hours, the graphite particles comprising the glucose oxidase (GOD-containing graphite particles) are air-dried.

The GOD-containing graphite particles obtained can be stored at 4° C.

Pasting material containing the charge-transfer mediator

Finally, the GOD-containing graphite particles is carefully mixed with paraffin oil containing the 1,1'-dimethylferrocene.

The paraffin oil (Merck art. 7161) in an amount corresponding to 0.6 ml=0.53 g per gram GOD-containing graphite is added to 1,1'-dimethylferrocene (Stream Chemical Inc. art. 26-1500) in an amount corresponding to 12.86 mg per gram GOD-containing graphite.

The 1,1'-dimethylferrocene is dissolved in the paraffin oil and is mixed with the GOD-containing graphite particles. An appropriate amount of n-pentane is added in order to facilitate the intimate mixing of the components and to ensure that the solution 1,1'-dimethylferrocene in paraffin oil is uniformly distributed in the GOD-containing graphite particles.

After mixing, the paste is left for one day to allow the n-pentane to evaporate and at suitable intervals stirred to facilitate the evaporation, and then the paste is ready to be filled into the electrode device, e.g. in vacuo.

EXAMPLE 4

Preparation of a sensor electrode comprising the glucose oxidase in an inactive form The preparation of sensor electrode wherein the glucose oxidase is present in an inactivated form is performed as described above, but the glucose oxidase is after immobilization on the graphite particles inactivated by exposing the GOD-containing graphite to 50° C. for 24 hours.

EXAMPLE 5

Preparation of the sensor electrode and filling the sensor electrode into a channel of the electrode device body The GOD-containing particles were prepared as described in Example 2.

The GOD-containing graphite is mixed with a sufficient amount of the non-polar pasting material, e.g. paraffin oil, in which the charge transfer mediator, e.g. 1,1'-dimethylferrocene has been dissolved. Preferably, the 1,1'-dimethylferrocene solution is about 0.1M in paraffin oil. The amount of the approximately 0.1M 1,1'-dimethylferrocene solution in paraffin oil is larger than the required and final amount in the sensor electrode. The reason therefor is that it should be possible to obtain a dispersion of GOD-containing graphite in the 1,1'-dimethylferrocene solution, which dispersion has a suitable consistency to allow the channel(s) in the electrode body to be filled. The excessive amount of the 1,1'-dimethylferrocene solution is easily removed after filling of the channel(s) of the sensor electrode in the electrode body by centrifugation. The amount used of the 1,1'-dimethylferrocene is preferably 3-4 times greater than the necessary amount to establish a final concentration of about 10-15 mg 1,1'-dimethylferrocene per gram GOD-containing graphite in the sensor electrode, and an amount of about 2-3 ml 1,1'-dimethylferrocene solution is normally used per gram GOD-containing graphite.

To fill the sensor electrode channels(s), the electrode device body is placed in a special holder having a small funnel-shaped reservoir at the top. The dispersion containing the GOD-containing graphite and the 1,1'-dimethylferrocene in paraffin oil solution is then poured into the reservoir. The electrode device body equipped with the filled reservoir is then centrifuged at about 15,000–50,000×g for about 5–30 min, the configuration preferably being performed at about 20,000×g for about 10 min, the electrode body device being positioned in an inverted position during centrifugation (i.e. that end of the device from which slices later are removed being uppermost). By the centrifugation the air is displaced from the channels and the GOD-containing graphite particles sediment, the interstices between the particles being filled with the 1,1'-dimethylferrocene in paraffin oil and the excess amount of 1,1'-dimethylferrocene in paraffin oil remaining as a supernatant in the upper part. After centrifugation the excess 1,1'-dimethylferrocene/paraffin oil is easily removed and the surface of the sensor electrode is levelled with the surface of the electrode device body by cutting off a suitable cross-sectional portion of the electrode device.

EXAMPLE 6

Preparation of a reference electrode comprising an Ag/AgCl electrode

At the bottom of the reference electrode channel of the electrode device body is placed an Ag/AgCl reference electrode and the channel is filled with an agarose gel containing a 1M solution of KCl.

Alternatively, the channel may be filled with a plastic embedding a powder of fine silver and silver chloride particles.

EXAMPLE 7

Measuring technique

In the following is given an example of the measuring technique. The measurement is performed with an apparatus according to the invention having a sensor electrode comprising 0.1M 1,1'-dimethylferrocene in paraffin oil and a reference electrode of Ag/AgCl in an agarose gel containing 1.0M KCl.

After having cut off a slice of the electrode device, a sample of the aqueous medium is applied on the fresh surface of the electrode device. The sample is preferably a sample of whole blood.

After 10-15 seconds, a constant potential (corresponding to 160 mV when a Ag/AgCl reference electrode comprising 1.0M KCl is used) is applied. After further 10-20 seconds, the currents are then integrated over 30 seconds. The charges measured are proportional to the concentration of the glucose in the sample.

Using 0.5M 1,1'-dimethylferrocene in paraffin oil, the measuring condition can be changed. Thus, the application of a constant potential (corresponding to 30 mV when a Ag/AgCl reference electrode working at a chloride ion concentration of 145 meq/l) is done substantially immediately. After about 1 second, the current is integrated over about 5 seconds. The charges measured are proportional to the concentration of the glucose in the sample.

Final result takes into account the known background (diffusion) current and a temperature coefficient of 4.5% per degree celsius.

I claim:

1. A method of amperometric detection of at least one constituent of a fluid sample of animal or human whole blood by means of a measuring apparatus containing an integrated electrode device including at least one enzyme sensor electrode and a reference electrode having an exposed surface part at a free end portion of the integrated electrode device and extending longitudinally through said end portion, said method being characterized in that the reference electrode used is an Ag/AgCl electrode working at a chloride ion concentration of about 145 meq/l and that before applying the sample on the exposed surface of the electrode device, said electrode device is moved longitudinally outward by an increment and subsequently the outer end section of said free end portion of the integrated electrode device is removed by means of removing means mounted movably on the measuring apparatus, so as to provide a new exposed surface part of the integrated electrode device, and that subsequently said new exposed surface part of the integrated electrode device is exposed to said fluid sample, so as to generate a measuring signal representative of said constituent of the sample.

2. A method according to claim 1, wherein the outer end section of the free end portion of the electrode device is removed by cutting.

3. A method according to claim 1 or 2, characterized in that said constituent is glucose.

4. A method according to claim 1, characterized in that there is used an enzyme sensor electrode in the form of a paste comprising electrically conductive particles and a pasting material, an oxidase enzyme and a charge-transfer mediator, and in that the charge-transfer mediator in its reduced form is dissolved in the pasting material in a concentration which is at least sufficient to ensure that the concentration of the charge-transfer mediator in its oxidized form is constant or close to constant at the exposed surface of the sensor electrode during the measurement, the charge-transfer mediator in its reduced form optionally further being present in undissolved form in the paste.

5. A method according to claim 4, characterized in that said paste is a paste comprising graphite particles and a non-polar pasting material.

6. A method according to claim 4 or 5, characterized in that the concentration of the reduced form of the charge-transfer mediator in the pasting material is from 0.01 to 0.5M.

7. A method according to claim 5, characterized in that an organometallic compound is used as a charge-transfer mediator, the reduced form of which is soluble in a non-polar pasting material.

8. A method according to claim 7, characterized in that the organometallic compound is a metallocene or a derivative thereof, preferably a ferrocene derivative.

9. A method according to claim 8, characterized in that the ferrocene derivative is 1,1'-dimethylferrocene.

10. A method according to claim 5, characterized in that said non-polar pasting material is used paraffin oil.

11. A method according to claim 1, characterized in that the measurement is performed at a potential between the sensor electrode and the Ag/AgCl reference electrode in communication with the fluid sample in a range of from 0 to 250 mV.

12. A method according to claim 11, characterized in that the measurement is performed at a potential between the sensor electrode and the Ag/AgCl reference electrode in a range of from 0 to 200 mV.

13. A method according to claim 12, characterized in that the measurement is performed at a potential of about 110 mV.

14. A method according to claim 12, characterized in that the measurement is performed at a potential of about 50 mV.

15. A method according to claim 12, characterized in that the measurement is performed at a potential of about 30 mV.

16. An electrode device for amperometric detection of at least one constituent of a fluid sample of animal or human whole blood, said device comprising an electrode body member (16) having a free end portion (21), at least one sensor electrode (18) extending axially through said end portion and having a cross-sectional area within said end portion, and a reference electrode which is uniform to close to uniform (19) also extending axially through the free end portion (21) of the electrode body member, each electrode being received in a bore extending longitudinally through the electrode body member and having an exposed surface part at the free end portion of the electrode body member, characterized in that the reference electrode is an Ag/AgCl electrode and that the sensor electrode is an electrically conductive electrode comprising a paste of electrically conductive particles and a pasting material containing an oxidase enzyme and a charge-transfer mediator, being distributed in the paste and in its reduced form being dissolved in the pasting material in a concentration which is at least sufficient to ensure that the concentration of the charge-transfer mediator in its oxidized form is constant or close to constant at the exposed surface of the sensor electrode during the measurement, the charge-transfer mediator in its reduced form optionally further being present in undissolved form in the paste.

17. An electrode device according to claim 16, characterized in that it further contains a counterelectrode (20) extending axially through the free end portion (21) of the electrode body member (16).

18. An electrode device according to claim 16, characterized in that the paste comprises graphite particles and a non-polar pasting material which is immiscible with water and which dissolves the charge-transfer mediator in its reduced form.

19. An electrode device according to claim 16, characterized in that the oxidase enzyme is glucose oxidase which is bonded or adsorbed to the electrically conductive particles, or which is bonded and adsorbed to the electrically conductive particles.

20. An electrode device according to claim 16, characterized in that the concentration of the reduced form of the charge-transfer mediator in the pasting material is from 0.01 to 1.5M.

21. An electrode device according to claim 16, characterized in that the non-polar pasting material is paraffin oil.

22. An electrode device according to claim 16, characterized in that the electrode body member is made from a polymeric material.

23. An electrode device according to claim 22, characterized in that the polymeric material is a mixture of high density polyethylene and low density polyethylene, the weight ratio between the amount of high density and low density polyethylene preferably being about 1.

24. An electrode device according to claim 16, characterized in that it comprises two sensor electrodes (18), an Ag/AgCl reference electrode (19) and a counter electrode (20).

25. An electrode device according to claim 24, characterized in that the two sensor electrodes are of the same type.

26. An electrode device according to claim 25, characterized in that the two sensor electrodes are different, one electrode comprising glucose oxidase in a catalytically active form, the other electrode comprising glucose oxidase in an inactivated form.

27. A measuring apparatus for measuring at least one constituent of a fluid sample of animal or human whole blood, characterized in that it comprises
   a body member (10) defining an outwardly open cavity (14) for receiving an electrode device (15) therein,
   removing means (27) mounted on the body member (10) so as to be movable in relation thereto along a path intersecting said cavity (14) for removing an outer end section from a free end portion of the electrode device (15) received in the cavity (14),
   means (30-34 and 37) for moving the electrode device outwardly by an increment each time the removing means has been operated,
   an electronic measuring circuitry (35) for processing measuring signals received from the electrode or electrodes of the electrode device, and
   connecting means for electrically connecting the electrode or electrodes of the electrode device to the electronic measuring circuitry when the electrode device is received in said cavity.

28. An apparatus according to claim 27, characterized in that said removing means define a cutting edge (28) for cutting the outer end section from the free end portion of the electrode device when the removing means are moved along said path.

29. An apparatus according to claim 27 or 28, characterized in that the removing means are mounted so as to be movable reciprocatingly along said path.

30. An apparatus according to claim 27, characterized in that the removing means are mounted on the apparatus body member so as to be rotatable in relation thereto.

31. An apparatus according claim 30, characterized in that it further comprises means for permitting rotation of the removing means in one direction only.

32. An apparatus according to claim 31, characterized in that said rotation permitting means comprise a ratchet mechanism.

33. An apparatus according to claim 27, characterized in that said moving means comprise a driving member driven by the movement of said removing means.

34. An apparatus according to claim 27, characterized in that the removing means are mounted on a lid-like member (11) which is movable to a closing, non-operative position.

35. An apparatus according to claim 27, characterized in that it further comprises
   a skin-puncturing member (46) mounted in the apparatus body member (10) so as to be movable between a retracted position and an extended position,
   biassing means (52, 53) for biassing the puncturing member toward its extended position, and
   releasable locking means (54) for retaining the puncturing member in its retracted position against the bias of the biassing means, whereby the puncturing member may perform a sudden skin-puncturing movement from its retracted to its extended position, when the locking means are released.

36. An apparatus according to claim 16, characterized in that it further comprises a visual display (36) for displaying the result of measurements performed by the electrode or electrodes of the electrode device.

37. An apparatus according to claim 27 wherein the removing means (27) is mounted on the body member (10) to move between a first position, in which the removing means (27) is laterally offset from the electrode device (15) to expose the electrode device (15) for use, and a second position, in which the removing means (27) is positioned to remove an outer end section from a free end portion of the electrode device (15).

38. An apparatus according to claim 27 wherein the electrode device moving means (30-34 and 37) positively moves the electrode device outwardly by a preselected distance each time the removing means (27) is operated.

39. An electrode device according to claim 16, characterized in that the oxidase enzyme is glucose oxidase which is bonded or absorbed to the electrically conductive particles.

40. A method according to claim 4 or 5, characterized in that the concentration of the reduced form of the charge-transfer mediator in the pasting material is from 0.05 to 1.0M.

41. A method according to claim 4 or 5, characterized in that the concentration of the reduced form of the charge-transfer mediator in the pasting material is from 0.07 to 0.7M.

42. A method according to claim 4 or 5, characterized in that the concentration of the reduced form of the charge-transfer mediator in the pasting material is from 0.04 to 0.7M.

43. A method according to claim 11, characterized in that the measurement is performed at a potential between the sensor electrode and the Ag/AgCl reference electrode in a range of from 10 to 150 mV.

44. A method according to claim 11, characterized in that the measurement is performed at a potential between the sensor electrode and the Ag/AgCl reference electrode in a range of from 20 to 120 mV.

45. An electrode device according to claim 16 characterized in that the concentration of the reduced form of the charge-transfer mediator in the pasting material is from 0.05 to 1.0M.

46. An electrode device according to claim 16 characterized in that the concentration of the reduced form of the charge-transfer mediator in the pasting material is from 0.07 to 0.7M.

47. An electrode device according to claim 16 characterized in that the concentration of the reduced form of the charge-transfer mediator in the pasting material is from 0.4 to 1.7M.

* * * * *

UNITED STATES PATENT AND TRADEMARK OFFICE
CERTIFICATE OF CORRECTION

PATENT NO. : 5,269,891
DATED : December 14, 1993
INVENTOR(S) : Fernand J.G. Colin It is certified that error appears in the above-indentified patent and that said Letters Patent is hereby corrected as shown below:

In column 3, line 6, after "samples" delete ",".

In column 4, line 3, delete "aspect" and substitute --aspects--.

In column 6, line 1, delete "like-like" and substitute --lid-like--.

In column 6, line 3, after "in" insert --a--.

In column 6, line 11, delete "toward" and substitute --towards--.

In column 6, line 44, delete "of" and substitute --or--.

In column 9, line 35, delete "slideable" and substitute --sliceable--.

In column 10, line 7, after "The" insert --longitudinal--.

In column 11, line 3 delete "by" and substitute --be--.

In column 12, line 23, delete the first occurrence of "it" and substitute --is--.

In column 12, line 39, delete "measuring" and substitute --measured--.

UNITED STATES PATENT AND TRADEMARK OFFICE
CERTIFICATE OF CORRECTION

PATENT NO. : 5,269,891
DATED : December 14, 1993
INVENTOR(S) : Fernand J.G. Colin Page 2 of 5

It is certified that error appears in the above-indentified patent and that said Letters Patent is hereby corrected as shown below:

In column 12, line 61, delete "Kcl" and substitute --KCl--.

In column 12, line 63, after "to" insert --a--.

In column 13, line 9, after "performed" delete"." insert --:--

In column 13, line 17, delete "p-toluenesulfonic" and substitute --p-toluenesulfonate--.

In column 13, line 68, delete "0.01" and substitute --0.1--.

In column 15, line 17, delete "b" and substitute --be--.

In column 16, line 3, delete "use din" and substitute --used in--.

In column 16, line 55, delete "$M_i$" and substitute --$M_c$--.

In column 16, line 63, delete "At" and substitute --As--.

In column 17, line 13, delete "specifies" and substitute --species--.

In column 17, line 43, delete "formed" and substitute --found--.

In column 18, line 25, after "$I_c$(" delete "-".

UNITED STATES PATENT AND TRADEMARK OFFICE
CERTIFICATE OF CORRECTION

PATENT NO. : 5,269,891
DATED : December 14, 1993
INVENTOR(S) : Fernand J.G. Colin It is certified that error appears in the above-indentified patent and that said Letters Patent is hereby corrected as shown below:

In column 18, line 26, after "2)" delete ",".

In column 18, line 29, delete the second occurrence of "aspect" and substitute --sensor--.

In column 18, line 31, delete "using" and substitute --usual--.

In column 18, line 31, delete "$CTM^{30}$" and substitute --$CTM^{+}$--.

In column 21, line 4, delete "2" and substitute --24--.

In column 23, line 6, delete "or" and substitute --of--.

In column 23, line 31, after "pin" insert --51--.

In column 24, line 66, after "64" delete ",".

In column 24, line 66, after "and" delete "-".

In column 25, line 8, delete the second occurrence of "of" and substitute --or--.

In column 28, line 13, delete "IC32" and substitute --IC2--.

UNITED STATES PATENT AND TRADEMARK OFFICE
CERTIFICATE OF CORRECTION

PATENT NO. : 5,269,891
DATED : December 14, 1993
INVENTOR(S) : Fernand J.G. Colin Page 4 of 5

It is certified that error appears in the above-indentified patent and that said Letters Patent is hereby corrected as shown below:

In column 28, line 60, delete "R2" and substitute --R21--.

In column 29, line 12, delete the second occurrence of "the".

In column 29, line 32, after "$E^2$" delete "-"

In column 30, line 41, delete "esc" and substitute --sec--.

In column 32, line 35, delete "working" and substitute --sensor--.

In column 32, line 45, after ")" insert --fixed--.

In column 34, line 55, after "within" insert --which--.

In column 35, line 1, after "exposed" insert --to--.

In column 35, line 3, delete "in" and substitute --into--.

In column 37, line 62, after "solution" insert --of--.

In column 38, line 49, delete "configuration" and substitute --centrifugation--.

UNITED STATES PATENT AND TRADEMARK OFFICE
CERTIFICATE OF CORRECTION

PATENT NO. : 5,269,891
DATED : December 14, 1993
INVENTOR(S) : Fernand J.G. Colin It is certified that error appears in the above-indentified patent and that said Letters Patent is hereby corrected as shown below:

IN THE CLAIMS

Col. 40:
In Claim 6, line 18, delete "0.5M" and substitute --1.5M--.

In Claim 16, line 54, after "portion," insert --which is uniform or close to uniform--.

In Claim 16, line 55, delete "which is uniform to close to uniform".

Col. 42:
In Claim 16, line 66, after "being" insert --uniformly--.

In Claim 35, line 35, delete "toward" and substitute --towards--.

Col. 43:
In Claim 42, line 7, delete "0.04" and substitute --0.4--.

Signed and Sealed this

Sixth Day of December, 1994

Attest:

BRUCE LEHMAN

Attesting Officer

Commissioner of Patents and Trademarks